(12) United States Patent
Suzuki

(10) Patent No.: US 10,076,275 B2
(45) Date of Patent: Sep. 18, 2018

(54) INFORMATION PROCESSING DEVICE, INFORMATION PROCESSING SYSTEM, AND PROGRAM

(71) Applicant: Sony Corporation, Tokyo (JP)

(72) Inventor: Masaru Suzuki, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/301,967

(22) PCT Filed: Apr. 3, 2015

(86) PCT No.: PCT/JP2015/060555
§ 371 (c)(1),
(2) Date: Oct. 5, 2016

(87) PCT Pub. No.: WO2015/159732
PCT Pub. Date: Oct. 22, 2015

(65) Prior Publication Data
US 2017/0202504 A1    Jul. 20, 2017

(30) Foreign Application Priority Data
Apr. 16, 2014   (JP) ................................. 2014-084291

(51) Int. Cl.
*G06K 9/00*     (2006.01)
*A61B 5/00*     (2006.01)
(Continued)

(52) U.S. Cl.
CPC ............ *A61B 5/443* (2013.01); *A61B 5/0077* (2013.01); *A61B 5/1032* (2013.01); *A61B 5/743* (2013.01);
(Continued)

(58) Field of Classification Search
USPC ....... 382/100, 103, 106, 108, 128–133, 154, 382/162, 168, 173, 181, 189, 199, 209,
(Continued)

(56) References Cited

U.S. PATENT DOCUMENTS

2006/0092315 A1* 5/2006 Payonk ................ A61B 5/0071
                                                          348/370
2007/0064985 A1   3/2007 Chhibber et al.
(Continued)

FOREIGN PATENT DOCUMENTS

JP    2008-289706 A   12/2008
JP    2009-006089 A   1/2009
(Continued)

*Primary Examiner* — Seyed Azarian
(74) *Attorney, Agent, or Firm* — Wolf, Greenfield & Sacks, P.C.

(57) ABSTRACT

The present technology relates to an information processing device, an information processing system, and a program which enable a state of pores to be understood in further detail.
A photographing unit photographs skin of a person irradiated with first light of a first wavelength band or second light of a second wavelength band different from the first wavelength band. A pore detecting unit detects pores in a first skin image, which is an image obtained by photographing the skin of the person irradiated with the first light. A porphyrin detecting unit detects a pore state of the skin of the person based on pixel values of a plurality of color components of each of pixels of a second skin image, which is an image obtained by photographing the skin of the person irradiated with second light. A display control unit distinguishes pores in which an abnormality is detected and normal pores based on a detection result of the pores and the pore state of the skin of the person and control display of the pore state of the skin of the person. The present technology can be applied to a system for analyzing a pore state of skin, for example.

19 Claims, 17 Drawing Sheets

(51) Int. Cl.
 *A61B 5/103* (2006.01)
 *H04N 5/222* (2006.01)
(52) U.S. Cl.
 CPC .... *A61B 5/7485* (2013.01); *A61B 2562/0233* (2013.01); *A61B 2576/02* (2013.01)
(58) Field of Classification Search
 USPC ....... 382/219, 224, 232, 254, 274, 276, 286, 382/291, 305, 312, 321; 606/9; 348/370; 709/203
 See application file for complete search history.

(56) References Cited

U.S. PATENT DOCUMENTS

| | | |
|---|---|---|
| 2007/0064989 A1 | 3/2007 | Chhibber et al. |
| 2008/0147053 A1* | 6/2008 | Kang .................. A61B 5/0071 606/9 |
| 2008/0194928 A1 | 8/2008 | Bandic et al. |
| 2009/0136101 A1 | 5/2009 | Chhibber et al. |
| 2009/0141956 A1 | 6/2009 | Chhibber et al. |
| 2009/0245603 A1* | 10/2009 | Koruga .................. A45D 44/00 382/128 |
| 2011/0301441 A1* | 12/2011 | Bandic ................. A61B 5/0059 600/306 |
| 2015/0186518 A1* | 7/2015 | Kusumoto ......... G06Q 30/0631 709/203 |

FOREIGN PATENT DOCUMENTS

| | | |
|---|---|---|
| JP | 2009-508648 A | 3/2009 |
| JP | 2011-509154 A | 3/2011 |

\* cited by examiner

INFORMATION PROCESSING DEVICE, INFORMATION PROCESSING SYSTEM, AND PROGRAM

CROSS-REFERENCE TO RELATED APPLICATIONS

This application is a National Stage of International Application No. PCT/JP 2015/060555, filed in the Japanese Patent Office as a Receiving office on Apr. 3, 2015,which claims priority to Japanese Patent Application Number 2014-084291,filed in the Japanese Patent Office on Apr. 16, 2014,each of which is hereby incorporated by reference in its entirety.

TECHNICAL FIELD

The present technology relates to an information processing device, an information processing system, and a program, and more particularly, to an information processing device, an information processing system, and a program which are suitable for use when a state of pores of a user's skin is presented.

BACKGROUND ART

In the past, techniques of performing detection of porphyrins by binarizing an image obtained by extracting a red (R) component from an image photographed by irradiating the skin of the user with ultraviolet (UV) light and then displaying a region in which porphyrins are detected, the number of detected porphyrins, and an area size in which porphyrins are detected have been proposed (for example, see Patent Literatures 1 and 2).

CITATION LIST

| Patent Literature | |
| --- | --- |
| Patent Literature 1: | JP 2007-152084A |
| Patent Literature 2: | JP 2009-494A |

SUMMARY OF INVENTION

Technical Problem

However, in the inventions disclosed in Patent Literatures 1 and 2, only the region in which porphyrins are detected is displayed. For this reason, for example, it is hard to detect whether there are normal pores in which no porphyrins are generated in a region in which no porphyrins are detected or whether or not there is a possibility that porphyrins are generated with no pores.

In this regard, it is an object of the present technology to enable the state of pores to be understood in further detail.

Solution to Problem

An information processing device according to a first aspect of the present technology includes a display control unit configured to distinguish pores in which an abnormality is detected and normal pores based on a detection result of pores and a pore state of the skin of a person and control display of the pore state of the skin of the person.

The display control unit may distinguish the pores in which an abnormality is detected and the normal pores and control display of a pore state image, which is an image indicating the pore state of the skin of the person.

The pores in which an abnormality is detected may include at least one of pores in which porphyrins are detected and pores in which porphyrin precursors are detected.

The display control unit may perform control such that the pore state image is displayed so that the pores in which porphyrins are detected and the pores in which the porphyrin precursors are detected are distinguished.

The display control unit may perform control such that the pore state image is displayed so that the pores in which porphyrins are detected and the pores in which the porphyrin precursors are detected are not distinguished.

The display control unit may perform control such that only pores of a selected type are displayed in the pore state image.

The pores in which an abnormality is detected may include at least one of pores in which porphyrins are detected and pores in which porphyrin precursors are detected.

The display control unit may control display of a graph indicating proportions of pores in which porphyrins and porphyrin precursors are detected and the normal pores or a graph indicating proportions of the pores in which porphyrins are detected, the pores in which porphyrin precursors are detected, and the normal pores.

The display control unit may perform control such that pores of a selected type in the graph are highlighted in a pore state image, which is an image indicating the state of the pores in the skin of the person.

The display control unit may perform control such that a graph having an axis indicating a porphyrin rate, which is the proportion of the pores in which porphyrins are detected, and an axis indicating a porphyrin precursor rate, which is the proportion of the pores in which porphyrin precursors are detected, is displayed, and positions on the graph corresponding to the porphyrin rate and the porphyrin precursor rate of the user are displayed.

The display control unit may control display of a graph indicating transition of a statistic related to at least one of the pores in which porphyrins are detected, the pores in which porphyrin precursors are detected, and the normal pores.

The information processing device may further include a pore detecting unit configured to detect pores in a first skin image, which is an image obtained by photographing the skin of the person irradiated with first light of a first wavelength band, and a state detecting unit configured to detect the pore state of the skin of the person based on pixel values of a plurality of color components of a second skin image obtained by photographing the skin of the person irradiated with second light of a second wavelength band different from the first wavelength band.

The first light may be white light, the second light may be UV light, and the state detecting unit may detect porphyrins and porphyrin precursors based on pixel values of R, G, and B components of each of pixels of the second skin image.

The state detecting unit may determine that porphyrins are generated in a region in which the pixel value of the R component is relatively larger than the pixel value of the G component, and the pixel value of the G component is relatively larger than the pixel value of the B component among regions of the second skin image corresponding to pores detected in the first skin image and determine that porphyrin precursors are generated in a region in which the pixel value of the R component is substantially equal to the pixel value of the G component, and the pixel values of the R component and the G component are relatively larger than the pixel value of the B component.

The state detecting unit may determine that porphyrins are generated in a region in which the pixel value of the R component is relatively larger than the pixel value of the G component, and the pixel value of the G component is relatively larger than the pixel value of the B component among regions in which pixels of a chromatic color are concentrated in the second skin image and determine that porphyrin precursors are generated in a region in which the pixel value of the R component is substantially equal to the pixel value of the G component, and the pixel values of the R component and the G component are relatively larger than the pixel value of the B component.

The information processing device may further include a correcting unit configured to delete a region in which no pores are detected in the first skin image from the region in which the porphyrins or the porphyrin precursors are determined to be generated.

A program according to the first aspect of the present technology causes a computer to execute a process including a display control step of distinguishing pores in which an abnormality is detected and normal pores based on a detection result of pores and a pore state of the skin of a person and controlling display of the pore state of the skin of the person.

An information processing system according to a second aspect of the present technology includes a photographing unit configured to photograph the skin of a person irradiated with first light of a first wavelength band or second light of a second wavelength band different from the first wavelength band, a pore detecting unit configured to detect pores in a first skin image, which is an image obtained by photographing the skin of the person irradiated with the first light, a state detecting unit configured to detect a pore state of the skin of the person based on pixel values of a plurality of color components of each of pixels of a second skin image, which is an image obtained by photographing the skin of the person irradiated with second light, and a display control unit configured to distinguish pores in which an abnormality is detected and normal pores based on a detection result of the pores and the pore state of the skin of the person and control display of the pore state of the skin of the person.

The display control unit may distinguish the pores in which an abnormality is detected and the normal pores and control display of a pore state image, which is an image indicating the pore state of the skin of the person.

The information processing system may further include a display unit configured to display the pore state image.

The first light may be white light, the second light may be UV light, the state detecting unit may detect porphyrins and porphyrin precursors based on pixel values of R, G, and B components of each of pixels of the second skin image, and the display control unit may distinguish between the normal pores and at least one of pore in which porphyrins are detected and pores in which porphyrin precursors are detected based on a detection result of porphyrins and porphyrin precursors of the skin of the person and control display of the pore state of the skin of the person.

The state detecting unit may determine that the porphyrins are generated in a region in which the pixel value of the R component is relatively larger than the pixel value of the G component, and the pixel value of the G component is relatively larger than the pixel value of the B component among regions of the second skin image corresponding to pores detected in the first skin image and determine that the porphyrin precursors are generated in a region in which the pixel value of the R component is substantially equal to the pixel value of the G component, and the pixel values of the R component and the G component are relatively larger than the pixel value of the B component.

The state detecting unit may determine that the porphyrins are generated in a region in which the pixel value of the R component is relatively larger than the pixel value of the G component, and the pixel value of the G component is relatively larger than the pixel value of the B component among regions in which pixels of a chromatic color are concentrated in the second skin image and determine that the porphyrin precursors are generated in a region in which the pixel value of the R component is substantially equal to the pixel value of the G component, and the pixel values of the R component and the G component are relatively larger than the pixel value of the B component.

The information processing system may include a photographing device including at least the photographing unit and an information processing device including at least the display control unit, and the pore detecting unit and the state detecting unit may be included in the photographing device or the information processing device.

An information processing system according to a third aspect of the present technology includes a photographing device including a photographing unit, a pore detecting unit, a porphyrin detecting unit, and a counting unit, and an information processing device including a display control unit, wherein the photographing unit photographs the skin of a person irradiated with white light or UV light having a predetermined wavelength, the pore detecting unit detects pores in a first skin image, which is an image obtained by photographing the skin of the person irradiated with the white light, the porphyrin detecting unit detects porphyrins and porphyrin precursors based on pixel values of R, G, and B components of each of pixels of a second skin image serving as an image obtained by photographing the skin of the person irradiated with the UV light, the counting unit counts the number of detected pores, the number of porphyrins, and the number of porphyrin precursors, and the display control unit controls display of data based on the number of pores, the number of porphyrins, and the number of porphyrin precursors.

In the first aspect of the present technology, the pore state of the skin of the person is displayed so that pores in which an abnormality is detected and normal pores are distinguished based on a detection result of pores and a pore state of the skin of a person.

In the second aspect of the present technology, the skin of a person irradiated with first light of a first wavelength band or second light of a second wavelength band different from the first wavelength band is photographed, pores in a first skin image, which is an image obtained by photographing the skin of the person irradiated with the first light is detected, a pore state of the skin of the person is detected based on pixel values of a plurality of color components of each of pixels of a second skin image, which is an image obtained by photographing the skin of the person irradiated with second light, and the pore state of the skin of the person is displayed so that pores in which an abnormality is detected and normal pores are distinguished based on a detection result of the pores and the pore state of the skin of the person.

In the third aspect of the present technology, the skin of a person irradiated with white light or UV light having a predetermined wavelength is photographed, pores in a white-light skin image, which is an image obtained by photographing the skin of the person irradiated with the white light, are detected, porphyrins and porphyrin precursors are detected based on pixel values of R, G, and B components of each of pixels of a UV-light skin image, which is an image obtained by photographing the skin of the person irradiated with the UV light, the number of detected pores, the number of porphyrins, and the number of porphyrin precursors are counted, and display of data is controlled based on the number of pores, the number of porphyrins, and the number of porphyrin precursors.

Advantageous Effects of Invention

According to the first to third aspects of the present technology, it is possible for the pore state to be understood in further detail.

DESCRIPTION OF EMBODIMENT(S)

Hereinafter, modes (hereinafter referred to as "embodiments") for carrying out the present technology will be described. The description will proceed in the following order.

1. First embodiment (example of detecting porphyrin using pore detection result)
2. Second embodiment (example of detecting porphyrin without using pore detection result)
3. Modified examples <1. First Embodiment>

First, an analysis system according to a first embodiment of the present technology will be described with reference to FIGS. 1 to 22.

{Configuration Example of Analysis System 1}

Figure 1:
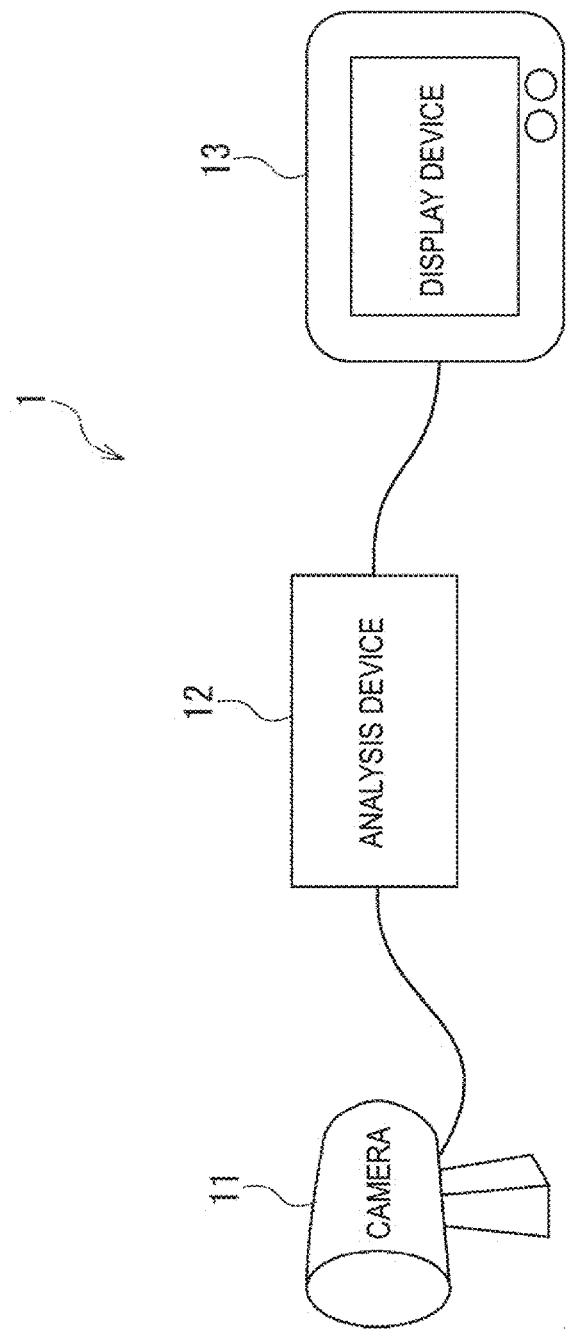
FIG. 1 is a diagram illustrating an analysis system according to a first embodiment of the present technology.

FIG. 1 illustrates an example configuration of devices of an analysis system 1 to which the present technology is applied.

In the analysis system 1, the skin of a user is photographed, the skin state of the user, particularly the pore state of the user, is analyzed based on an obtained skin image, and an analysis result is presented to the user. The analysis system 1 is configured to include a camera 11, an analysis device 12, and a display device 13.

The camera 11 is configured with a photographing device capable of photographing a wavelength band of UV light in addition to visible light. The camera 11 photographs the skin of the user serving as a target whose pore state is analyzed, and supplies an obtained skin image to the analysis device 12.

For example, the analysis device 12 is configured with a dedicated device, a personal computer, or a mobile terminal (for example, a smartphone, a tablet, a mobile phone, or the like). The analysis device 12 may be implemented by a server (for example, a server on a cloud) or the like connected to a network (not illustrated). The analysis device 12 analyzes the skin state of the user, particularly the pore state of the user, based on the skin image acquired from the camera 11, and causes the analysis result to be displayed on the display device 13.

For example, the display device 13 is configured with a dedicated display or a display with which a personal computer, a tablet, a smartphone, or the like is equipped. The display device 13 displays the analysis result of the skin state of the user, particularly the pore state of the user, under control of the analysis device 12.

Communication between the camera 11 and the analysis device 12 or communication between the analysis device 12 and the display device 13 may be wired communication or wireless communication.

{Example of Functional Configuration of Analysis System}

Figure 2:
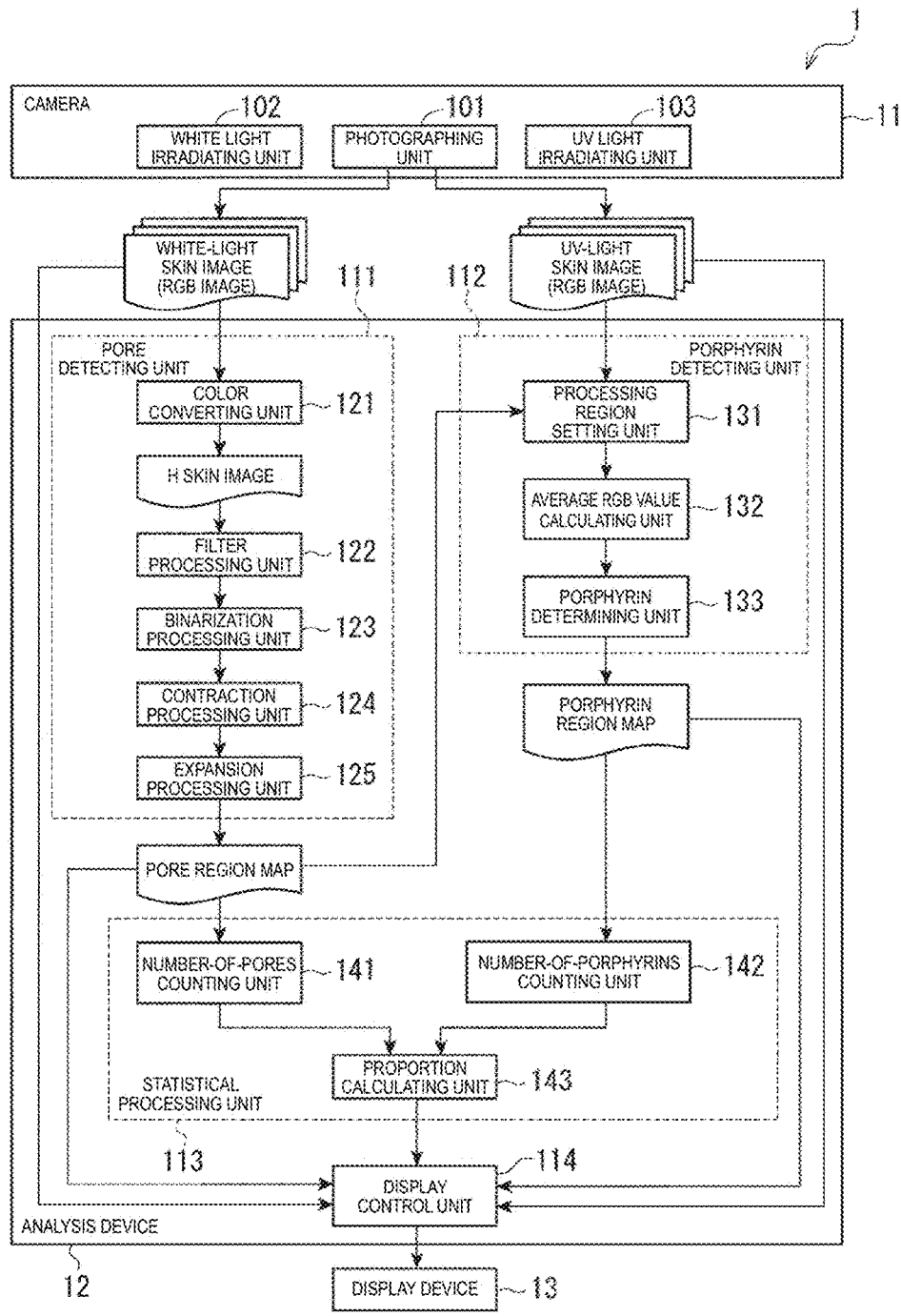
FIG. 2 is a block diagram illustrating an example of a functional configuration of the analysis system according to the first embodiment.

FIG. 2 is a block diagram illustrating an example of a functional configuration of the analysis system 1.

The camera 11 is configured to include a photographing unit 101, a white light irradiating unit 102, and a UV light irradiating unit 103.

The photographing unit 101 is configured to include an image sensor such as a CMOS image sensor, a CCD image sensor, or the like having sensitivity to the wavelength band of the UV light in addition to the visible light. The photographing unit 101 photographs a region serving as an analysis target (hereinafter referred to as an "analysis region") of the skin of the user in a state in which the skin of the user is irradiated with the white light emitted from the white light irradiating unit 102. The photographing unit 101 supplies an RGB image obtained as a result of photographing (hereinafter referred to as a "white-light skin image") to a color converting unit 121 of a pore detecting unit 111 and a display control unit 114 of the analysis device 12. The photographing unit 101 photographs the analysis region of the skin of the user in the state in which the skin of the user is irradiated with the UV light emitted from the UV light irradiating unit 103. The photographing unit 101 supplies an image obtained as a result of photographing (hereinafter referred to as a "UV-light skin image") to a processing region setting unit 131 of a porphyrin detecting unit 112 and the display control unit 114 of the analysis device 12.

The photographing unit 101 preferably has a resolution with which pores of the face of a person can be vividly photographed. Preferably, the photographing unit 101 can perform close-up photography.

For example, the white light irradiating unit 102 is configured with a white light emitting diode (LED), a camera flash, or the like, and irradiates the skin of the user with the white light.

For example, the UV light irradiating unit 103 is configured with a light source that emits the UV light or the like, and irradiates the skin of the user with the UV light. The wavelength band of the UV light irradiated from the UV light irradiating unit 103 is set to a range of 350 to 400 nm included in a wavelength band of near-ultraviolet light.

Preferably, the white light irradiating unit 102 and the UV light irradiating unit 103 are installed at substantially the same position and irradiate the skin of the user with the illumination light in substantially the same direction.

The analysis device 12 is configured to include the pore detecting unit 111, the porphyrin detecting unit 112, a statistical processing unit 113, and the display control unit 114.

The pore detecting unit 111 detects the pores in the analysis region based on the white-light skin image. The pore detecting unit 111 is configured to include the color converting unit 121, a filter processing unit 122, a binarization processing unit 123, a contraction processing unit 124, and an expansion processing unit 125.

The color converting unit 121 converts a color space of the white-light skin image which is the RGB image into an HSV color space, and generates an image (hereinafter referred to as an "H skin image") having H (hue) components of the white-light skin image. The color converting unit 121 supplies the generated H skin image to the filter processing unit 122.

The filter processing unit 122 performs a predetermined filter process on the H skin image, and extracts a low-frequency component of the H skin image. The filter processing unit 122 supplies the H skin image that has undergone the filter process to the binarization processing unit 123.

The binarization processing unit 123 converts the H skin image into a binary image by performing a binarization process on the H skin image. The binarization processing unit 123 supplies the binary image to the contraction processing unit 124.

The contraction processing unit 124 performs a contraction process of a morphology operation on the binary image. The contraction processing unit 124 supplies the binary image that has undergone the contraction process to the expansion processing unit 125.

The expansion processing unit 125 performs an expansion process of the morphology operation on the binary image, and generates a pore region map indicating a position distribution of the pores in the analysis region. The expansion processing unit 125 supplies the generated pore region map to the processing region setting unit 131 of the porphyrin detecting unit 112, a number-of-pores counting unit 141 of the statistical processing unit 113, and the display control unit 114.

The porphyrin detecting unit 112 detects the pore state in the analysis region, particularly porphyrins, based on the UV-light skin image and the pore region map. The porphyrin detecting unit 112 is configured to include the processing region setting unit 131, an average RGB value calculating unit 132, and a porphyrin determining unit 133.

The processing region setting unit 131 sets regions corresponding to pore regions shown in the pore region map as a processing region serving as a target that undergoes a porphyrin determination in the UV-light skin image. The processing region setting unit 131 supplies the UV-light skin image and information indicating the set processing region to the average RGB value calculating unit 132.

The average RGB value calculating unit 132 calculates an average value of a pixel value of each of R, G, and B components in each processing region of the UV-light skin image. The average RGB value calculating unit 132 supplies the UV-light skin image and information indicating a calculation result of the average value to the porphyrin determining unit 133.

The porphyrin determining unit 133 performs the porphyrin determination on each processing region of the UV-light skin image, and detects a region in which porphyrins are generated (hereinafter referred to as a "porphyrin region") and a region in which precursors of porphyrins are generated (hereinafter referred to as a "porphyrin precursor region"). The porphyrin determining unit 133 generates the porphyrin region map indicating position distributions of the porphyrin region and the porphyrin precursor region in the analysis region, and supplies the porphyrin region map to a number-of-porphyrins counting unit 142 of the statistical processing unit 113 and the display control unit 114.

The statistical processing unit 113 performs a calculation process of calculating a statistical value indicating the pore state of the user based on the pore region map and the porphyrin region map. The statistical processing unit 113 is configured to include the number-of-pores counting unit 141, the number-of-porphyrins counting unit 142, and a proportion calculating unit 143.

The number-of-pores counting unit 141 counts the number of pore regions in the analysis region (hereinafter referred to as "the number of pores") based on the pore region map, and supplies a counting result to the proportion calculating unit 143.

The number-of-porphyrins counting unit 142 counts the number of porphyrin regions (hereinafter referred to as "the number of porphyrins") and the number of porphyrin precursor regions (hereinafter referred to as "the number of porphyrin precursors") in the analysis region based on the porphyrin region map, and supplies a counting result to the proportion calculating unit 143.

The proportion calculating unit 143 calculates a proportion of each type of pore of the user based on the counting results of the number of pores, the number of porphyrins, and the number of porphyrin precursors, and supplies a calculation result to the display control unit 114.

The display control unit 114 causes the analysis result of the pore state of the user to be displayed on the display device 13 based on the white-light skin image, the UV-light skin image, the pore region map, the porphyrin region map, and the calculation result of the proportion of each type of pore.

{Analysis Process}

Next, an analysis process performed by the analysis system 1 will be described with reference to a flowchart of FIG. 3.

In step S1, the analysis system 1 performs a pore detection process. Here, the pore detection process will be described in detail with reference to a flowchart of FIG. 4.

In step S51, the camera 11 photographs the white-light skin image. Specifically, the photographing unit 101 photographs the analysis region in the state in which the analysis region of the skin of the user and a region around the analysis region are irradiated with the white light emitted from the white light irradiating unit 102. For example, the analysis region is set in the entire nose, a part of a nose (for example, a side part of a nose), a part of a cheek adjacent to a nose, the forehead, the scalp, the entire face, the entire head, and the like. The photographing unit 101 supplies the white-light skin image obtained as a result of photographing to the color converting unit 121 and the display control unit 114.

Figure 5:
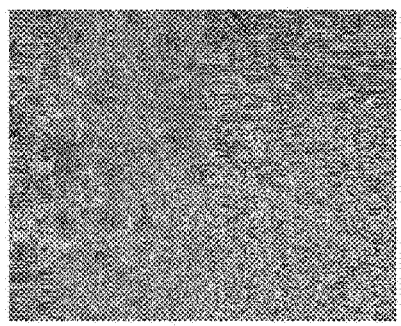
FIG. 5 is a diagram illustrating an example of a white-light skin image.

FIG. 5 illustrates an example a white-light skin image obtained by photographing a side part of a nose. The white-light skin image is illustrated in grayscale, but an actual white-light skin image is a color RGB image.

For example, the white-light skin image may be photographed under natural light that is a sort of white light without using the white light illuminating unit 102.

In step S52, the color converting unit 121 performs color conversion of the white-light skin image. In other words, the color converting unit 121 converts the color space of the white-light skin image serving as the RGB image into the HSV color space, and generates an image (the H skin image) of the H (hue) component of the white-light skin image. The color converting unit 121 supplies the generated H skin image to the filter processing unit 122.

A value of the H component of each pixel is obtained by the following Formulas (1) to (3) based on pixel values of R (red), G (green), and B (blue) components of each pixel.

[Math. 1]

$$H = \begin{cases} 60 \times \frac{G-B}{MAX-MIN} + 0 & \text{if } MAX = R \quad (1) \\ 60 \times \frac{B-R}{MAX-MIN} + 120 & \text{if } MAX = G \quad (2) \\ 60 \times \frac{R-G}{MAX-MIN} + 240 & \text{if } MAX = B \quad (3) \end{cases}$$

Formula (1) is used for a pixel in which the pixel value of the R component is highest, Formula (2) is used for a pixel in which the pixel value of the G component is highest, and Formula (3) is used for a pixel in which the pixel value of the B component is highest. In each Formula, R, G, and B indicate the pixel values of the R, G, and B components, MAX indicates a maximum value among the pixel values of R, G, and B of each pixel, and MIN indicates a minimum value among the pixel values of R, G, and B of each pixel. Further, when a value of the right sides of Formulas (1) to (3) is less than 0, a value obtained by adding 360 to the value is set as the pixel value of the H component of the pixel.

Figure 6:
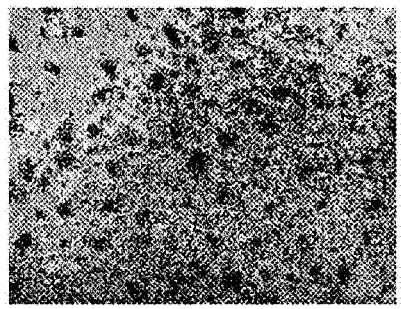
FIG. 6 is a diagram illustrating an example of an H skin image.

FIG. 6 illustrates an example of an H skin image obtained by performing the color conversion on the white-light skin image of FIG. 5. A high-frequency component such as noise or a fine edge is included in the H skin image.

In step S53, the filter processing unit 122 performs the filter process on the H skin image. In other words, the filter processing unit 122 extracts the low-frequency component of the H skin image by applying a low-pass filter to the H skin image. For example, when the H skin image is 1280× 1024 pixels, an average filter of 9×9 taps is used. The filter processing unit 122 supplies the H skin image that has undergone the filter process to the binarization processing unit 123.

Figure 7:
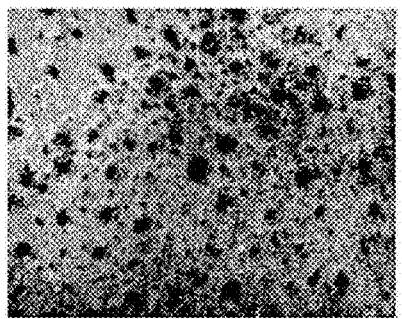
FIG. 7 is a diagram illustrating an example of an H skin image after a filter process.

FIG. 7 illustrates an example of an H skin image obtained by performing the filter process on the H skin image of FIG. 6. The H skin image is an image obtained by removing noise, a fine edge, and the like from the H skin image of FIG. 6.

In step S54, the binarization processing unit 123 performs the binarization process. In other words, the binarization processing unit 123 converts the H skin image that has undergone the filter process into the binary image by setting 1 as a pixel value of a pixel in which the value of the H component is less than or equal to a predetermined threshold value Hth and setting 0 as a pixel value of a pixel in which the value of the H component is larger than the threshold value Hth. For example, the value of the threshold value Hth is set to 64.8. The binarization processing unit 123 supplies the obtained binary image to the contraction processing unit 124.

Figure 8:
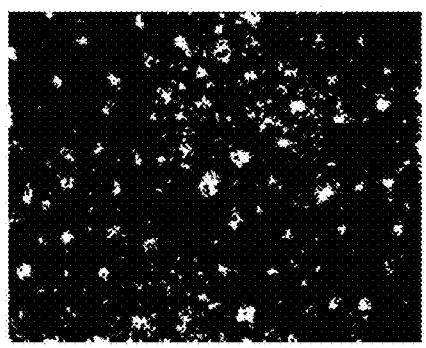
FIG. 8 is a diagram illustrating an example of a binary image.

FIG. 8 illustrates an example of a binary image obtained from the H skin image of FIG. 7 that has undergone the filter process. In the binary image, a region in which there are pores is indicated by a bright white point having a certain size. A non-pore region is also included among the bright white points.

In step S55, the contraction processing unit 124 repeats the contraction process a predetermined number of times. For example, the contraction processing unit 124 consecutively repeats the contraction process of the morphology operation on the binary image using a disk-like structuring element having a radius of 2 to 4 three times. The contraction processing unit 124 supplies the binary image that has undergone the contraction process to the expansion processing unit 125.

Figure 9:
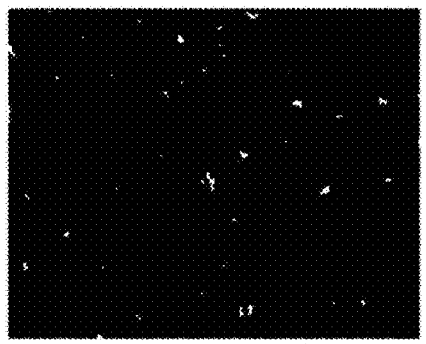
FIG. 9 is a diagram illustrating an example of a binary image after a contraction process.

FIG. 9 illustrates an example of a binary image obtained by performing the contraction process on the binary image of FIG. 8 a predetermined number of times. By performing the contraction process, a small bright white point different from the pore region is removed from the binary image.

In step S56, the expansion processing unit 125 repeats the expansion process a predetermined number of times. For example, the expansion processing unit 125 consecutively repeats the expansion process of the morphology operation on the binary image that has undergone the contraction process using a disk-like structuring element having a radius of 2 to 5 three times. The expansion processing unit 125 supplies the binary image that has undergone the expansion process to the processing region setting unit 131, the number-of-pores counting unit 141, and the display control unit 114 as the pore region map. Thereafter, the pore detection process ends.

Figure 10:
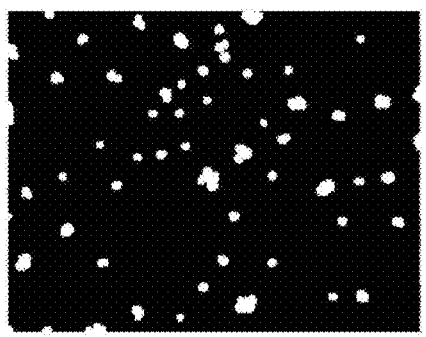
FIG. 10 is a diagram illustrating an example of a pore region map.

FIG. 10 illustrates an example of a pore region map obtained by performing the expansion process on the binary image of FIG. 9 that has undergone the contraction process. In the pore region map, each bright white point indicates the position of the pore region. By performing the expansion process, the size of the pore region contracted in the contraction process is restored to an original size.

In the process of steps S55 and S56, it is possible to arbitrarily change the number of morphology operations and the size and the shape of the structuring element. The above-described pore detection process is an example, and the pore region may be detected by another method.

Referring back to FIG. 3, in step S2, the analysis system 1 performs the porphyrin detection process. Here, the porphyrin detection process will be described in detail with reference to a flowchart of FIG. 11.

In step S101, the camera 11 photographs the UV-light skin image. Specifically, the photographing unit 101 photographs the analysis region in the state in which the analysis region of the skin of the user and a region around the analysis region are irradiated with the UV light emitted from the UV light irradiating unit 103. At this time, the white-light skin image and the UV-light skin image are preferably obtained by photographing substantially the same region in substantially the same direction. The photographing unit 101 supplies the UV-light skin image obtained as a result of photographing to the processing region setting unit 131 and the display control unit 114.

Figure 12:
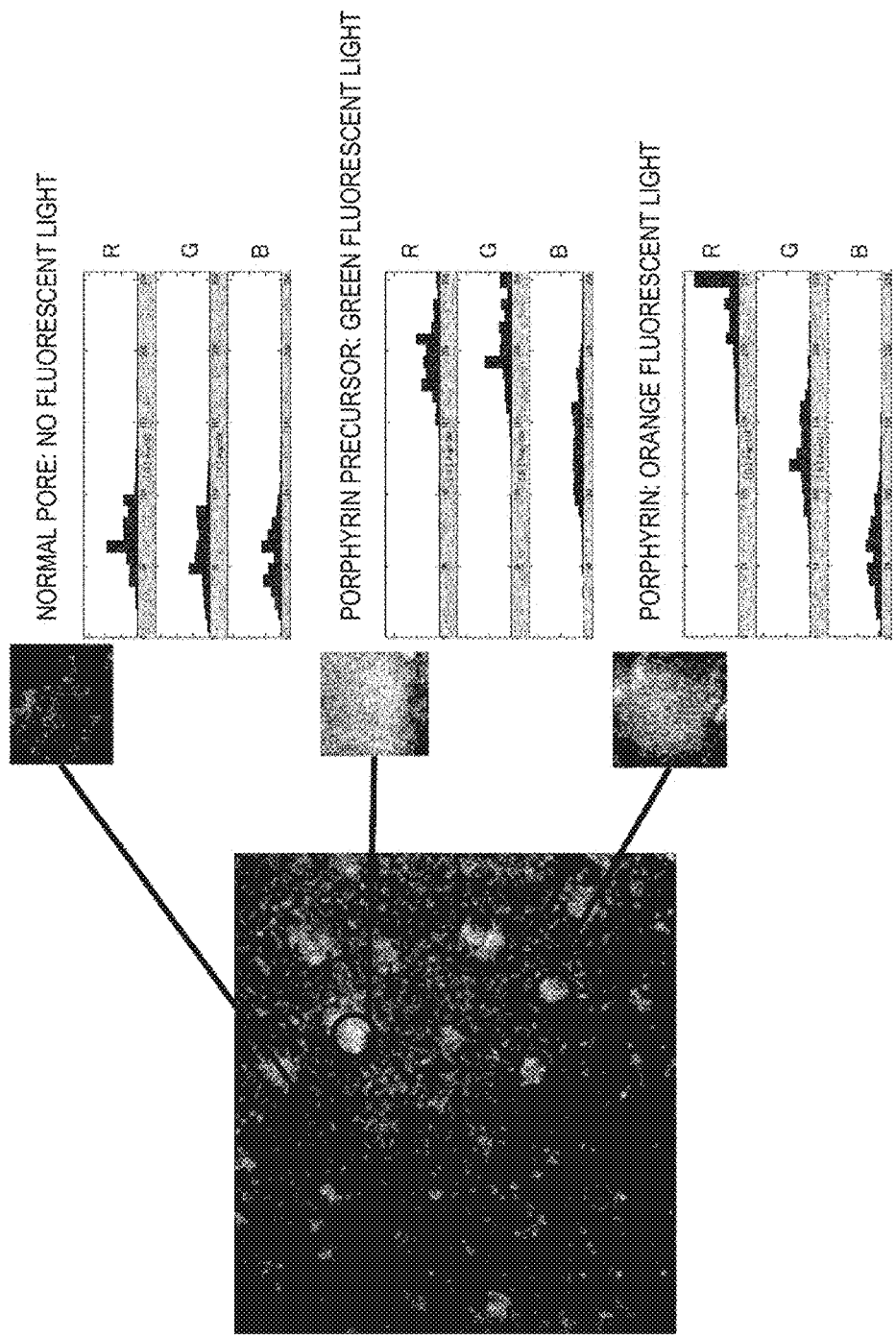
FIG. 12 is a diagram illustrating an example of a UV-light skin image.
Figure 13:
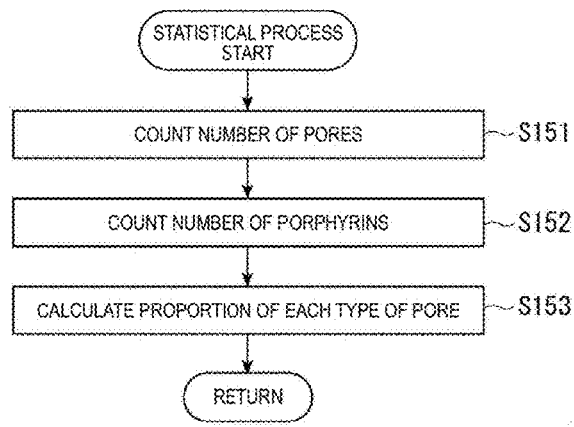
FIG. 13 is a flowchart for describing a statistical process in detail.

FIG. 12 illustrates an example of the UV-light skin image. The UV-light skin image is illustrated in grayscale, but an actual UV-light skin image is a color RGB image. Here, in order to facilitate understanding of a description, an example of a UV-light skin image obtained by photographing a different position from the white-light skin image of FIG. 5 is illustrated.

FIG. 12 illustrates an example of a histogram indicating the distribution of the pixel values of the R, G, and B components in a normal pore region in which neither porphyrins nor porphyrin precursors are generated, the porphyrin precursor region, and the porphyrin region.

Here, when the skin of a person is irradiated with the UV light having the wavelength band of 350 to 400 nm, fluorescent light of a different color is emitted according to the pore state. Specifically, the normal pore region typically becomes a dark region in which no fluorescent light is emitted. Thus, in the normal pore region, the pixel values of the R, G, and B components are typically small and have substantially the same distribution.

Green fluorescent light is typically emitted from the porphyrin precursor region. Thus, in the porphyrin precursor region, the pixel values of the R, G, and B components are typically relatively larger than in the normal pore region. The pixel values of the R component and the G component have substantially the same distribution, and the pixel value of the B component is relatively smaller than the pixel values of the R component and the G component.

Orange fluorescent light is typically emitted from the porphyrin region. Thus, in the porphyrin region, the pixel value of the R component is largest, and the pixel value of the B component is smallest. The pixel value of the R component is relatively larger than in the porphyrin precursor region, the pixel value of the G component is relatively larger than in normal pores and relatively smaller than in the porphyrin precursor region, and the pixel value of the B component has substantially the same distribution as the normal pores.

In step S102, the processing region setting unit 131 sets the processing region. Specifically, the processing region setting unit 131 sets a region of the UV-light skin image corresponding to each pore region shown in the pore region map as the processing region. The processing region setting unit 131 supplies the UV-light skin image and information indicating the set processing region to the average RGB value calculating unit 132.

In step S103, the average RGB value calculating unit 132 calculates an average of the R, G, and B components of each processing region. Specifically, the average RGB value calculating unit 132 calculates the average value of the pixel values of the R, G, and B components of the pixels in each processing region. The average RGB value calculating unit 132 supplies the UV-light skin image and the calculation result of the average value to the porphyrin determining unit 133.

In step S104, the porphyrin determining unit 133 performs the porphyrin determination. Specifically, first, the porphyrin determining unit 133 determines whether or not each processing region satisfies the following determination Formula (4):

$$\max\{\text{avg}R, \text{avg}G\} - \text{avg}B \geq \text{TH1} \qquad (4)$$

avgR, avgG, and avgB indicate the average values of the pixel values of the R, G, and B components in the processing region. TH1 indicates a predetermined threshold value.

Then, the porphyrin determining unit 133 determines that the processing region that does not satisfy the determination Formula (4) is the normal pore region. In other words, the processing region in which a difference between the average value of the pixel value of the B component and the larger one of the average value of the pixel value of the R component and the average value of the pixel value of the G component is less than the threshold value TH1 is determined to be the normal pore region. Thus, the processing region in which the difference in the distribution of the pixel values of the R, G, and B components is small is determined to be the normal pore region.

The porphyrin determining unit 133 determines whether or not each processing region that satisfies the determination Formula (4) satisfies the following determination Formula (5).

$$\text{avg}R - \text{avg}G \geq \text{TH2} \qquad (5)$$

TH2 indicates a predetermined threshold value.

Then, the porphyrin determining unit 133 determines that the processing region satisfying the determination Formula (5) is the porphyrin region. In other words, the processing region in which the difference between the average value of the pixel value of the B component and the larger one of the average value of the pixel value of the R component and the average value of the pixel value of the G component is larger than or equal to the threshold value TH1, and a difference between the average value of the pixel value of the R component and the average value of the pixel value of the G component is larger than or equal to the threshold value TH2 is determined to be the porphyrin region. Thus, the processing region in which the pixel value of the R component is relatively larger than the pixel value of the G component, and the pixel value of the G component is relatively larger than the pixel value of the B component is determined to be the porphyrin region.

On the other hand, the porphyrin determining unit 133 determines that the processing region that does not satisfy the determination Formula (5) is the porphyrin precursor region. In other words, the processing region in which the difference between a larger one of the average value of the pixel value of the R component and the average value of the pixel value of the G component and the average value of the pixel value of the B component is larger than or equal to the threshold value TH1, and the difference between the average value of the pixel value of the R component and the average value of the pixel value of the G component is less than the threshold value TH2 is determined to be the porphyrin precursor region. Thus, the processing region in which the pixel value of the R component and the pixel value of the G component are substantially equal, and the pixel value of the R component and the pixel value of the G component are relatively larger than the pixel value of the B component is determined to be the porphyrin precursor region.

Since the porphyrin determination is performed based on only the magnitude relation of the average values of the pixel values of the R, G, and B components, for example, even when emission tends to be dark, a type of pore can be determined with a high degree of accuracy.

Then, the porphyrin determining unit 133 generates the porphyrin region map indicating the position distribution of the porphyrin region and the porphyrin precursor region in the analysis region, and supplies the generated porphyrin region map to the number-of-porphyrins counting unit 142 and the display control unit 114. Thereafter, the porphyrin detection process ends.

The porphyrin determination may be performed using another statistical value (for example, a median value) indicating the distributions of the pixel values of the R component, the G component, and the B component in the processing region instead of the average value.

Referring back to FIG. 3, in step S3, the statistical processing unit 113 performs a statistical process. Here, the statistical process will be described in detail with reference to FIG. 13.

In step S151, the number-of-pores counting unit 141 counts the number of pores. In other words, the number-of-pores counting unit 141 counts the number of pores in the analysis region based on the pore region map. The number-of-pores counting unit 141 supplies a counting result of the number of pores to the proportion calculating unit 143.

In step S152, the number-of-porphyrins counting unit 142 counts the number of porphyrins. In other words, the number-of-porphyrins counting unit 142 counts the number of porphyrins and the number of porphyrin precursors in the analysis region based on the porphyrin region map. The number-of-porphyrins counting unit 142 supplies a counting result of the number of porphyrins and the number of porphyrin precursors to the proportion calculating unit 143.

In step S153, the proportion calculating unit 143 calculates a proportion of each type of pore. For example, the proportion calculating unit 143 calculates an abnormal pore rate, a porphyrin rate, a porphyrin precursor rate, and a normal pore rate using the following Formulas (6) to (9):

$$\text{abnormal pore rate (\%)} = (\text{number of porphyrins} + \text{number of porphyrin precursors})/\text{total number of pores} \times 100 \quad (6);$$

$$\text{porphyrin rate (\%)} = \text{number of porphyrins/total number of pores} \times 100 \quad (7);$$

$$\text{porphyrin precursor rate (\%)} = \text{number of porphyrin precursors/total number of pores} \times 100 \quad (8); \text{ and}$$

$$\text{normal pore rate (\%)} = 100 - \text{abnormal pore rate} \quad (9).$$

The total number of pores is the total number of pore regions detected in the analysis region.

Thus, the abnormal pore rate indicates a proportion that the abnormal pore regions (the porphyrin region and the porphyrin precursor region) occupy among the pore regions in the analysis region. The porphyrin rate indicates a proportion in which the porphyrin region occupies among the pore regions in the analysis region. The porphyrin precursor rate indicates a proportion that the porphyrin precursor region occupies among the pore regions in the analysis region. The abnormal pore rate indicates a sum of the porphyrin rate and the porphyrin precursor rate. The normal pore rate indicates a proportion that the normal pore region (the pore region in which neither porphyrins nor porphyrin precursors are generated) occupies among the pore regions in the analysis region.

Then, the proportion calculating unit 143 supplies the calculation result to the display control unit 114. Thereafter, the statistical process ends.

Referring back to FIG. 3, in step S4, the display device 13 displays the analysis result under control of the display control unit 114. In other words, the display control unit 114 causes the analysis result of the pore state of the user to be displayed on the display device 13 based on the white-light skin image, the UV-light skin image, the pore region map, the porphyrin region map, and the calculation result of the proportion of each type of pore. Thereafter, the analysis process ends.

Figure 14:
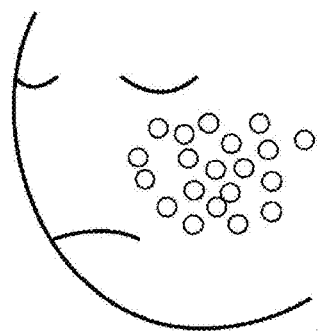
FIG. 14 is a diagram schematically illustrating an example of a pore region map.
Figure 15:
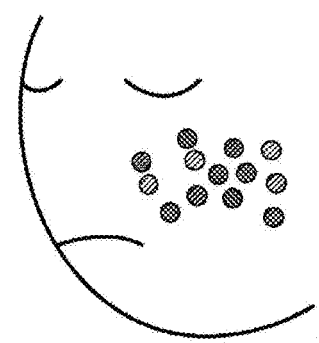
FIG. 15 is a diagram schematically illustrating an example of a porphyrin region map.

Here, a display example of the analysis result will be described with reference to FIGS. 14 to 22. An example in which the pore region map schematically illustrated in FIG. 14 is obtained through the pore detection process, and the porphyrin region map schematically illustrated in FIG. 15 is obtained through the porphyrin detection process will be described. A white circle in the pore region map of FIG. 14 indicates the pore region, and in FIG. 15, a shaded circle indicates the porphyrin region, and a hatched circle indicates the porphyrin precursor region.

Figure 16:
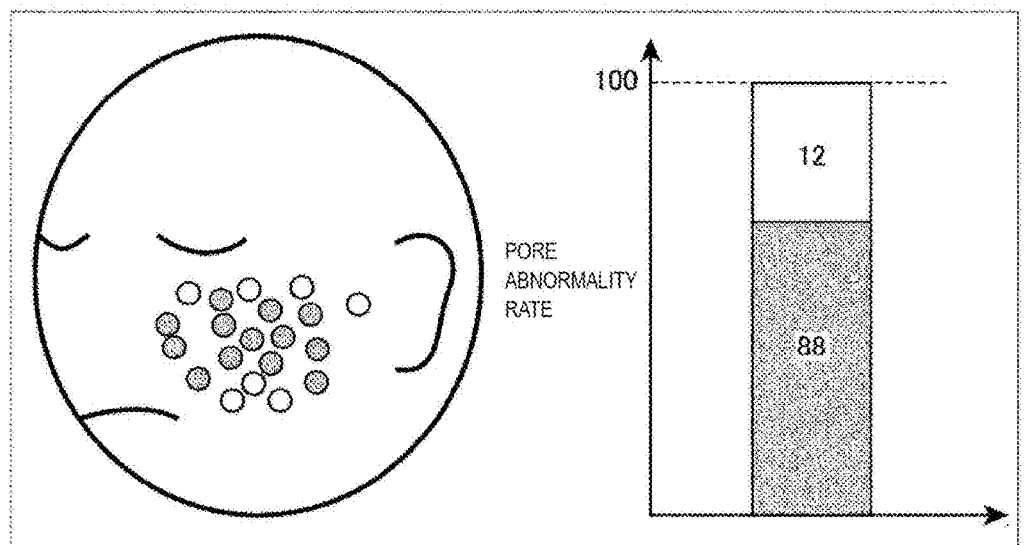
FIG. 16 is a diagram illustrating a first display example of an analysis result.

FIG. 16 schematically illustrates a first display example of the analysis result. A face image indicating the pore state of the user (hereinafter referred to as a "pore state image") is displayed on the left of a screen. For example, the pore state image is an image in which a position and a type of each detected pore are shown on the white-light skin image. In other words, a position of each detected pore is displayed on the white-light skin image through a predetermined mark such as a circle or a point. A mark in which a shape, a pattern, a display effect, or the like differs according to each type of pore is displayed so that a type of pore can be easily distinguished. For example, in this example, normal pores are indicated by white circles, and abnormal pores in which porphyrins or porphyrin precursors are generated are indicated by circles of a predetermined pattern.

As the face image used for the pore state image, in addition to the white-light skin image that is actually photographed, for example, an artificial image such as computer graphics or an illustration may be used.

Figure 17:
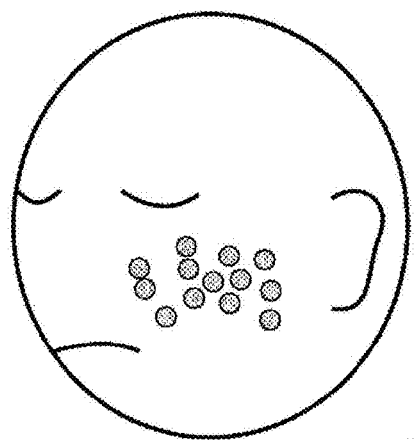
FIG. 17 is a diagram illustrating a display example of an analysis result according to a related art.

In the related art, only positions of abnormal pores are displayed as illustrated in FIG. 17. Thus, it is difficult for the user to understand whether, for example, there are normal pores or there are no pores in a region in which there are no abnormal pores.

On the other hand, in the example of FIG. 16, normal pores are displayed in addition to abnormal pores, and thus the user can understand the pore state of his/her skin in further detail. For example, the user can simply recognize the distribution of all detected pores or the distribution of normal pores and abnormal pores.

For example, by diagnosing the user continuously and comparing a previous pore state image with a current pore state image, the user can easily understand a normal region, a region in which the pore state has improved, a region in which the pore state has worsened, a region in which there are no pores, and the like.

Further, a pre analysis service provider can present the user with, for example, pore care effects to be understood specifically and easily.

A graph indicating a proportion of each type of each pore (hereinafter referred to as a "pore proportion graph") is displayed on the right of the screen. Specifically, in the pore proportion graph, the proportion of the abnormal pores and the normal pores is indicated by a bar graph together with a specific numerical value. In this example, the normal pores occupy 12 percent, and the abnormal pores occupy 88 percent. Thus, the user can understand his/her pore state through a specific numerical value.

Further, for example, when each item of the pore proportion graph is selected by a click, a touch, or the like, a pore corresponding to the selected item is highlighted in the pore state image. For example, when an item of an abnormal pore is selected in the pore proportion graph, a mark indicating the abnormal pore is highlighted in the pore state image. As a highlighting method, for example, an arbitrary method such as a color change, enlargement, or a blinking display can be employed.

Preferably, a mark indicating a type of each pore in the pore state image and each item of the pore proportion graph match in a color, a pattern, a display effect, or the like for each type of pore. In this case, the user can easily associate each pore in the pore state image with an item in the pore proportion graph.

Figure 18:
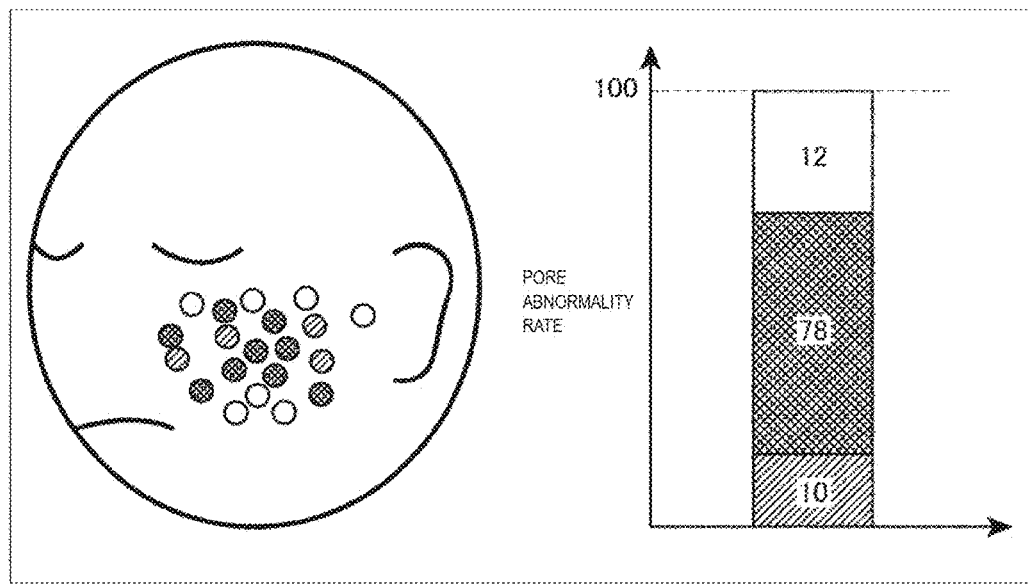
FIG. 18 is a diagram illustrating an analysis result according to a modified example of the first display example.

FIG. 18 schematically illustrates a modified example of the first display example of the analysis result. In this example, similarly to the example of FIG. 16, the pore state image is displayed on the left, and the pore proportion graph is displayed on the right. However, in this example, in the pore state image and the pore proportion graph, pores in which porphyrins are detected are distinguished from pores in which porphyrin precursors are detected.

Specifically, in the pore state image, the pores in which porphyrins are detected and the pores in which porphyrin precursors are detected are indicated by different marks. In other words, the pore in which a porphyrin is detected is indicated by a circle of a shaded pattern, and the pore in which a porphyrin precursor is detected is indicated by a circle of a hatched pattern. Thus, the user can understand the abnormal pore distribution while distinguishing the pores in which porphyrins are generated from the pores in which porphyrin precursors are generated.

In the pore proportion graph, the pores in which porphyrins are detected (the porphyrin rate) and the pores in which porphyrin precursors are detected (the porphyrin precursor rate) are displayed as separate items. In this example, the normal pores occupy 12 percent, the pores in which porphyrins are detected occupy 78 percent, and the pores in which porphyrin precursors are detected occupy 10 percent.

Further, similarly to the example of FIG. 16, when an item is selected in the pore proportion graph, a pore corresponding to the selected item is highlighted in the pore state image.

In this example, a mark indicating a type of each pore in the pore state image and an item of the pore proportion graph preferably match in a color, a pattern, a display effect, or the like for each type of pore.

Figure 19:
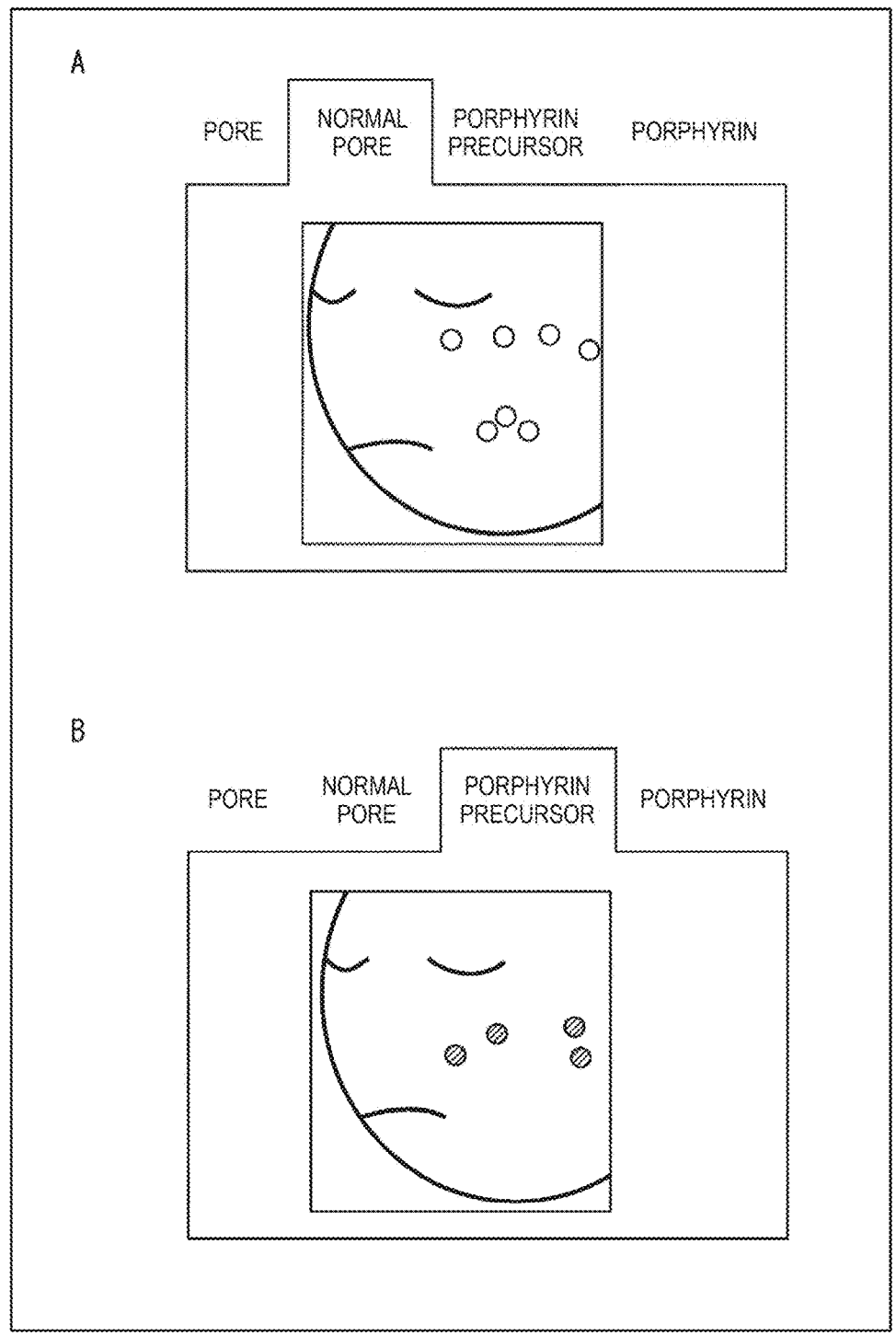
FIG. 19 is a diagram illustrating a second display example of an analysis result.

FIG. 19 schematically illustrates a second display example of the analysis result. In this example, tabs of "pore," "normal pore," "porphyrin precursor," and "porphyrin" are displayed on an upper portion of a screen. A pore state image similar to those of FIGS. 16 and 18 is displayed under a line of tabs.

In this example, a type of pore corresponding to the selected tab is displayed in the pore state image. Specifically, when the "pore" tab is selected, a pore state image similar to FIG. 18 is displayed. In other words, in the pore state image, the normal pores, the pores in which porphyrins are detected, and the pores in which porphyrin precursors are detected are displayed to be distinguished from one another. When the "normal pore" tab is selected, the normal pores are displayed in the pore state image as illustrated in A of FIG. 19. When the "porphyrin precursor" tab is selected, the pores in which porphyrin precursors are detected are displayed in the pore state image as illustrated in B of FIG. 19. When the "porphyrin" tab is selected, the pores in which porphyrins are detected are displayed in the pore state image, although this is not illustrated. Thus, the user can check the distribution of respective types of pores together or individually.

Figure 20:
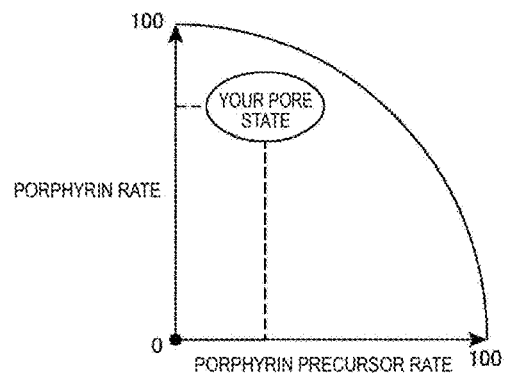
FIG. 20 is a diagram illustrating a third display example of an analysis result.

FIG. 20 schematically illustrates a third display example of the analysis result. In this example, a current position of the pore state of the user is illustrated in a two dimensional graph in which a horizontal axis indicates the porphyrin precursor rate, and a vertical axis indicates the porphyrin rate. For example, similarly to the example of FIG. 18, when the porphyrin precursor rate is 10 percent, and the porphyrin rate is 78 percent, the current position of the pore state of the user is illustrated on coordinates (10,78) of the graph as illustrated in FIG. 20.

When all pores are normal pores, the current position of the pore state of the user is illustrated on the origin (0,0). Thus, the current position of the pore state of the user is displayed at a position that is closer to the origin when the number of normal pores increases and gets farther from the origin when the number of abnormal pores increases. Thus, the user can understand his/her current pore state (for example, whether his/her skin is healthy or unhealthy) rapidly and intuitively.

Figure 21:
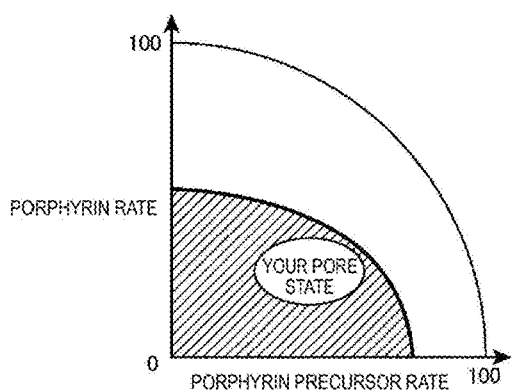
FIG. 21 is a diagram illustrating a modified example of the third display example of an analysis result.

FIG. 21 schematically illustrates a modified example of the third display example of the analysis result. In this example, a region (a hatched region in FIG. 21) in which most persons of the same generation as the user are distributed is illustrated on a graph of FIG. 20. This region is a region in which a predetermined percentage (for example, 95 percent) of persons among persons of the same generation as the user are included according to data accumulated in the analysis system 1, including the origin of the graph. In other words, this region is a region in which a predetermined percentage of persons in the descending order are included when persons of the same generation as the user are lined up in the order in which the pore state is healthy. Thus, when the current position of the pore state of the user is displayed outside this region, the pore state of the user is understood to be unhealthier than persons of the same generation.

Figure 22:
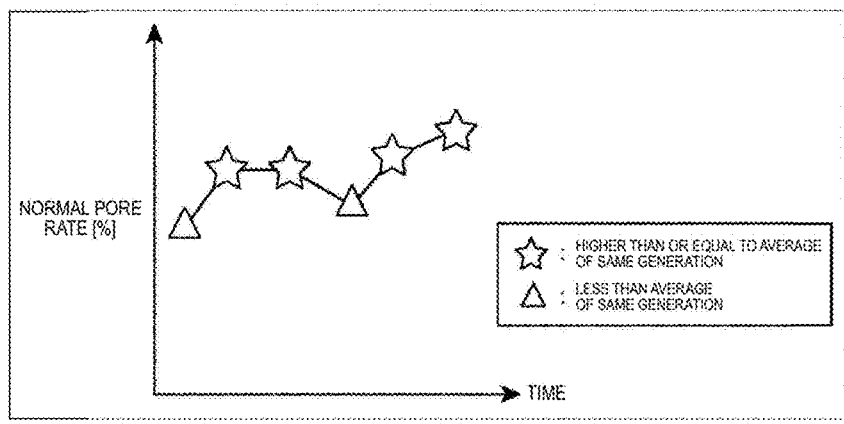
FIG. 22 is a diagram illustrating a fourth display example of an analysis result.

FIG. 22 schematically illustrates a fourth display example of the analysis result. In this example, chronological transition of the normal pore rate of the user is illustrated on a graph in which a horizontal axis indicates time, and a vertical axis indicates the normal pore rate. A unit of the time axis is set to days, weeks, months, years, or the like. In this graph, a plot indicating the normal pore rate of the user has a star shape when the normal pore rate is higher than or equal to an average of the same generation as the user and a triangle when the normal pore rate is lower than an average of the same generation as the user. Thus, the user can easily understand whether or not his/her skin is healthier than persons of the same generation together with a transition in his/her skin state. Further, the user can understand, for example, a progression rate at which the pore state gets worse or the pore care effects through a specific index.

Transition of data is indicated based on a statistic related to at least one of the pores in which porphyrins are detected, the pores in which porphyrin precursors are detected, and the normal pores in addition to the normal pore rate. For example, transition of the abnormal pore rate, the porphyrin rate, the porphyrin precursor rate, the number of pores, the number of porphyrins, the number of porphyrin precursors, the number of normal pores, and the like may be displayed. Further, transition of two or more statistics may be simultaneously displayed.

As a result, the user can understand the pore state of his/her skin in further detail. Further, since the pore state is intuitively displayed, the user can easily understand the pore state of his/her skin. In addition, the service provider can accurately explain the pore state of the user so that he/she can easily understand it.

The porphyrin determination is performed based on the pixel values of the R, G, and B components of the white-light skin image, and thus it is possible to identify the normal pores, the pores in which porphyrins are generated, and the pores in which the porphyrin precursors are generated with a high degree of accuracy.

<2. Second Embodiment>

Next, an analysis system according to a second embodiment of the present technology will be described with reference to FIGS. 23 to 26. In the second embodiment, the pore detection process and the porphyrin detection process are performed in parallel.

{Example Configuration of Analysis System 201}

Figure 23:
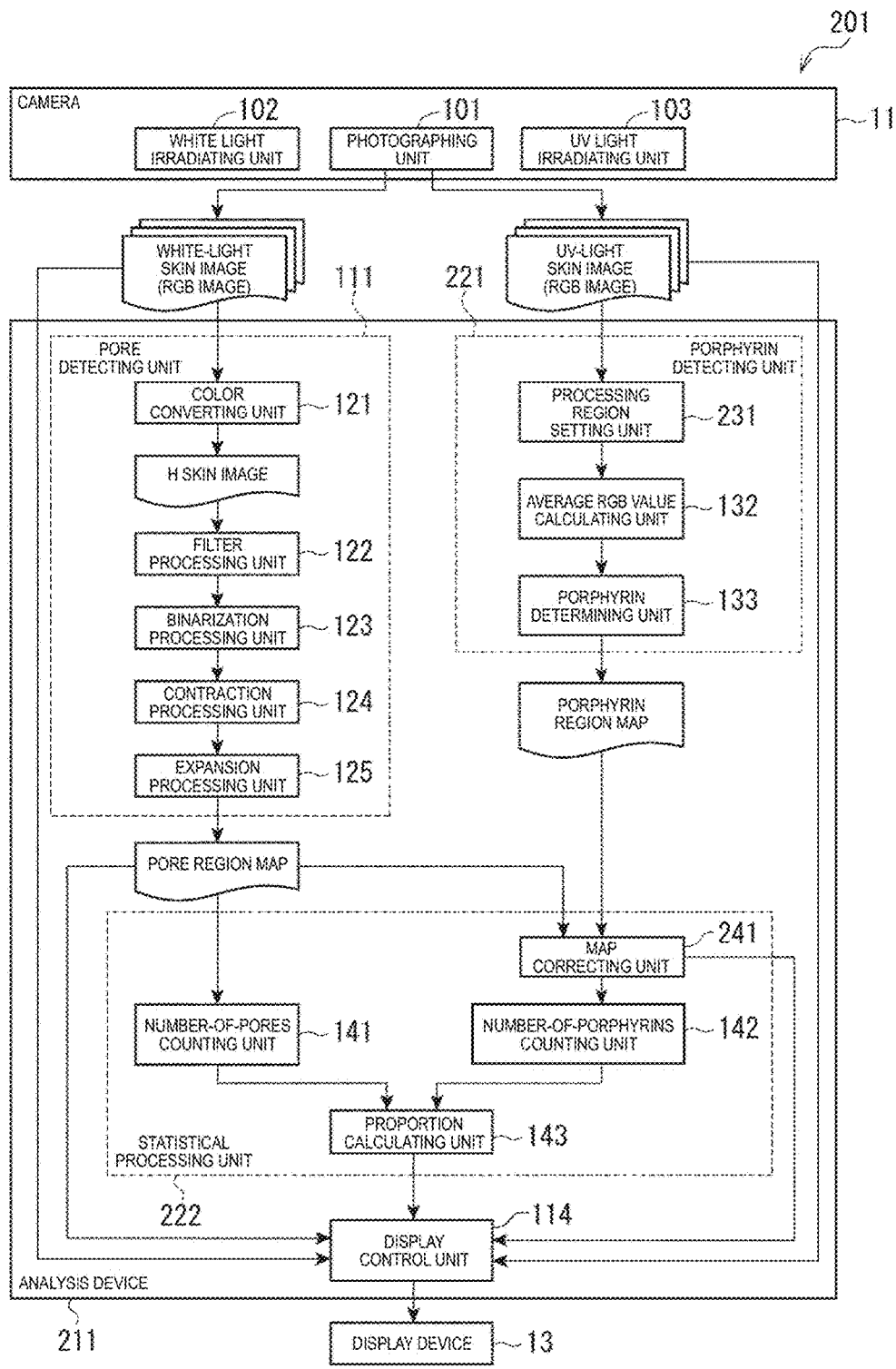
FIG. 23 is a block diagram illustrating an example of a functional configuration of an analysis system according to a second embodiment.

FIG. 23 illustrates an example configuration of the analysis system 201. In FIG. 23, parts corresponding to those in FIG. 2 are denoted by the same reference numerals, and repeated description of parts in which processing is the same will be appropriately omitted.

The analysis system 201 differs from the analysis system 1 of FIG. 2 in that an analysis device 211 is disposed instead of the analysis device 12. The analysis device 211 differs from the analysis device 12 in that a porphyrin detecting unit 221 and a statistical processing unit 222 are disposed instead of the porphyrin detecting unit 112 and the statistical processing unit 113. The porphyrin detecting unit 221 differs from the porphyrin detecting unit 112 in that a processing region setting unit 231 is disposed instead of the processing region setting unit 131. The statistical processing unit 222 differs from the statistical processing unit 113 in that a map correcting unit 241 is added.

The processing region setting unit 231 sets a processing region serving as a porphyrin determination target in the UV-light skin image without using the pore region map. The processing region setting unit 231 supplies the UV-light skin image and information indicating the set processing region to the average RGB value calculating unit 132.

The map correcting unit 241 acquires the pore region map from the expansion processing unit 125, and acquires the porphyrin region map from the porphyrin determining unit 133. Then, the map correcting unit 241 corrects the porphyrin region map based on the pore region map, and supplies the corrected porphyrin region map to the number-of-porphyrins counting unit 142 and the display control unit 114.

{Analysis Process}

Figure 24:
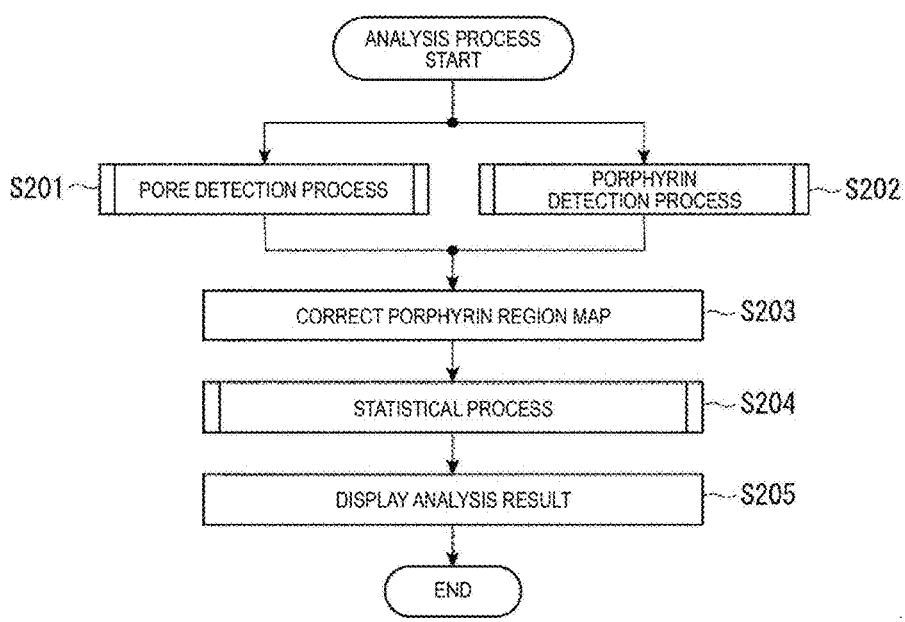
FIG. 24 is a flowchart for describing an analysis process according to the second embodiment.
Figure 25:
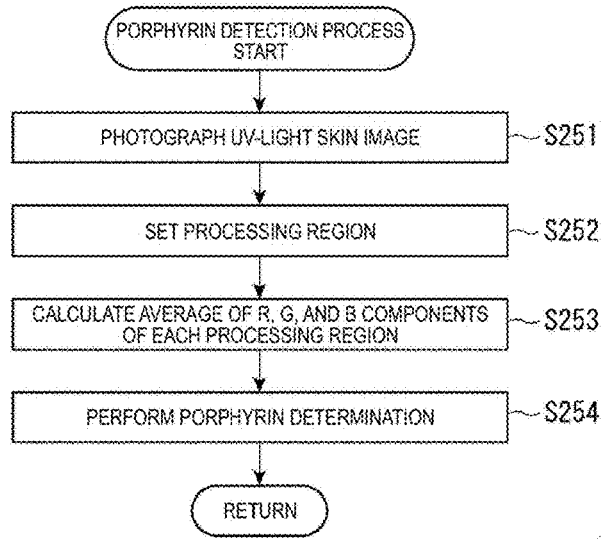
FIG. 25 is a flowchart for describing a porphyrin detection process according to the second embodiment in detail.

Next, an analysis process performed by the analysis system 201 will be described with reference to a flowchart of FIG. 24.

Figure 3:
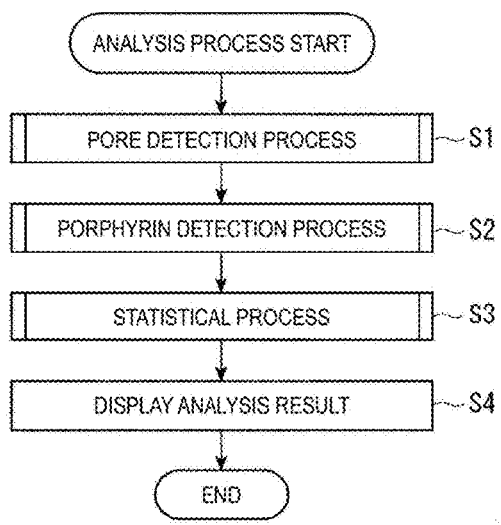
FIG. 3 is a flowchart for describing an analysis process according to the first embodiment.
Figure 4:
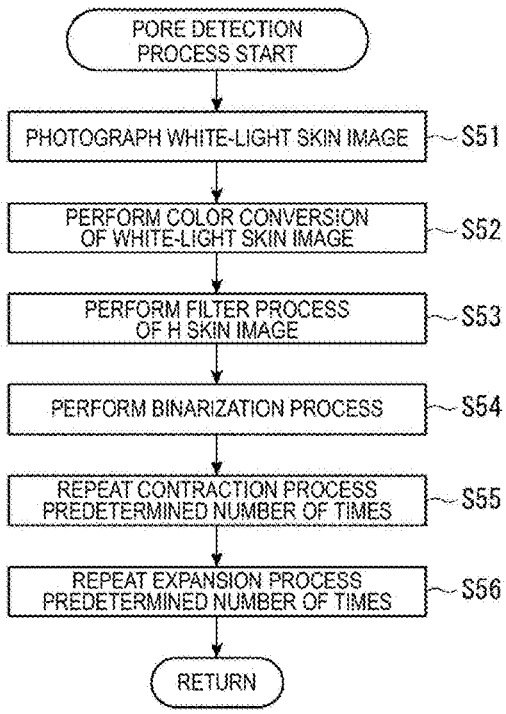
FIG. 4 is a flowchart for describing a pore detection process in detail.

In step S201, the pore detection process is performed, similarly to the process of step S1 of FIG. 3, and the process proceeds to step S203. The expansion processing unit 125 supplies the pore region map obtained as a result of the pore detection process to the number-of-pores counting unit 141, the map correcting unit 241, and the display control unit 114.

In step S202, the analysis system 201 performs the porphyrin detection process, and the process proceeds to step S203. Here, the porphyrin detection process will be described in detail with reference to a flowchart of FIG. 25.

Figure 11:
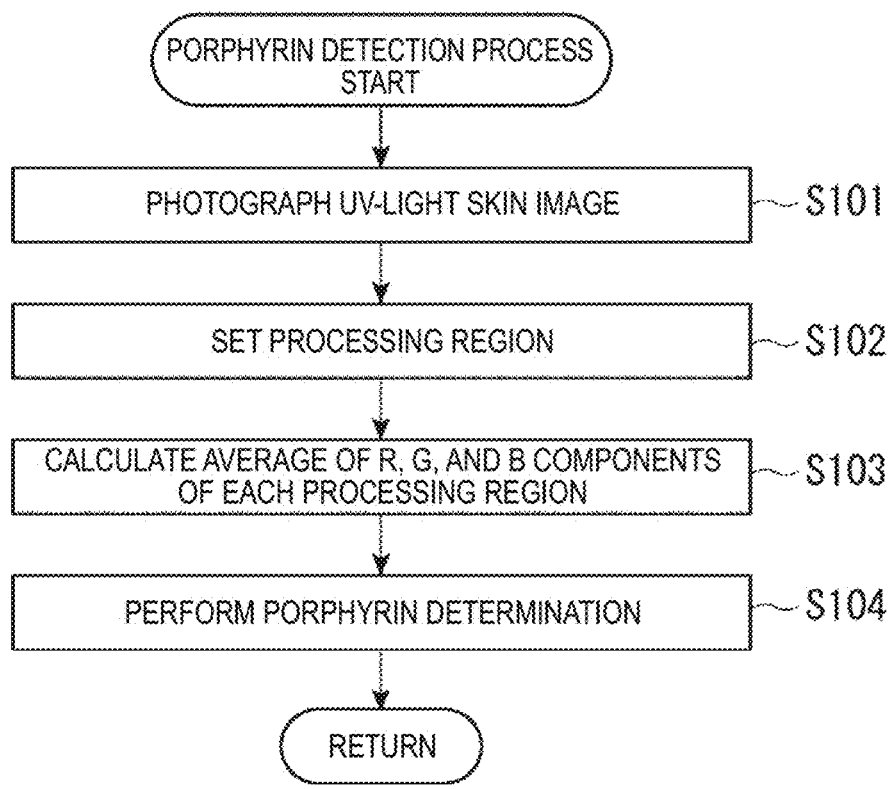
FIG. 11 is a flowchart for describing a porphyrin detection process according to the first embodiment in detail.

In step S251, the UV-light skin image is photographed, similarly to the process of step S101 of FIG. 11.

In step S252, the processing region setting unit 231 sets the processing region. Specifically, the processing region setting unit 231 classifies pixels of the UV-light skin image according to whether or not each pixel is a chromatic color, and segments the pixel determined to be chromatic colors. Thus, each region in which the pixels determined to be chromatic colors are concentrated is set as the processing region. The processing region setting unit 131 supplies a calculation result of the processing region to the average RGB value calculating unit 132.

In step S253, similarly to the process of step S103 of FIG. 11, an average of the R, G, and B components of each processing region is calculated.

In step S254, similarly to the process of step S104 of FIG. 11, the porphyrin determination is performed, and the porphyrin detection process ends. The porphyrin determining unit 133 supplies the generated porphyrin region map to the map correcting unit 241.

The pore detection process and the porphyrin detection process may be performed in parallel or may be performed sequentially. When the pore detection process and the porphyrin detection process are sequentially performed, any one of the processes may be performed first.

Referring back to FIG. 3, in step S203, the map correcting unit 241 corrects the porphyrin region map. Specifically, the map correcting unit 241 compares the porphyrin region and the porphyrin precursor region in the porphyrin region map with the pore region in the pore region map. Then, the map correcting unit 241 determines that the porphyrin region and the porphyrin precursor region in which there is no corresponding pore region are low in reliability of a detection result, and deletes the porphyrin region and the porphyrin precursor region from the porphyrin region map.

Figure 26:
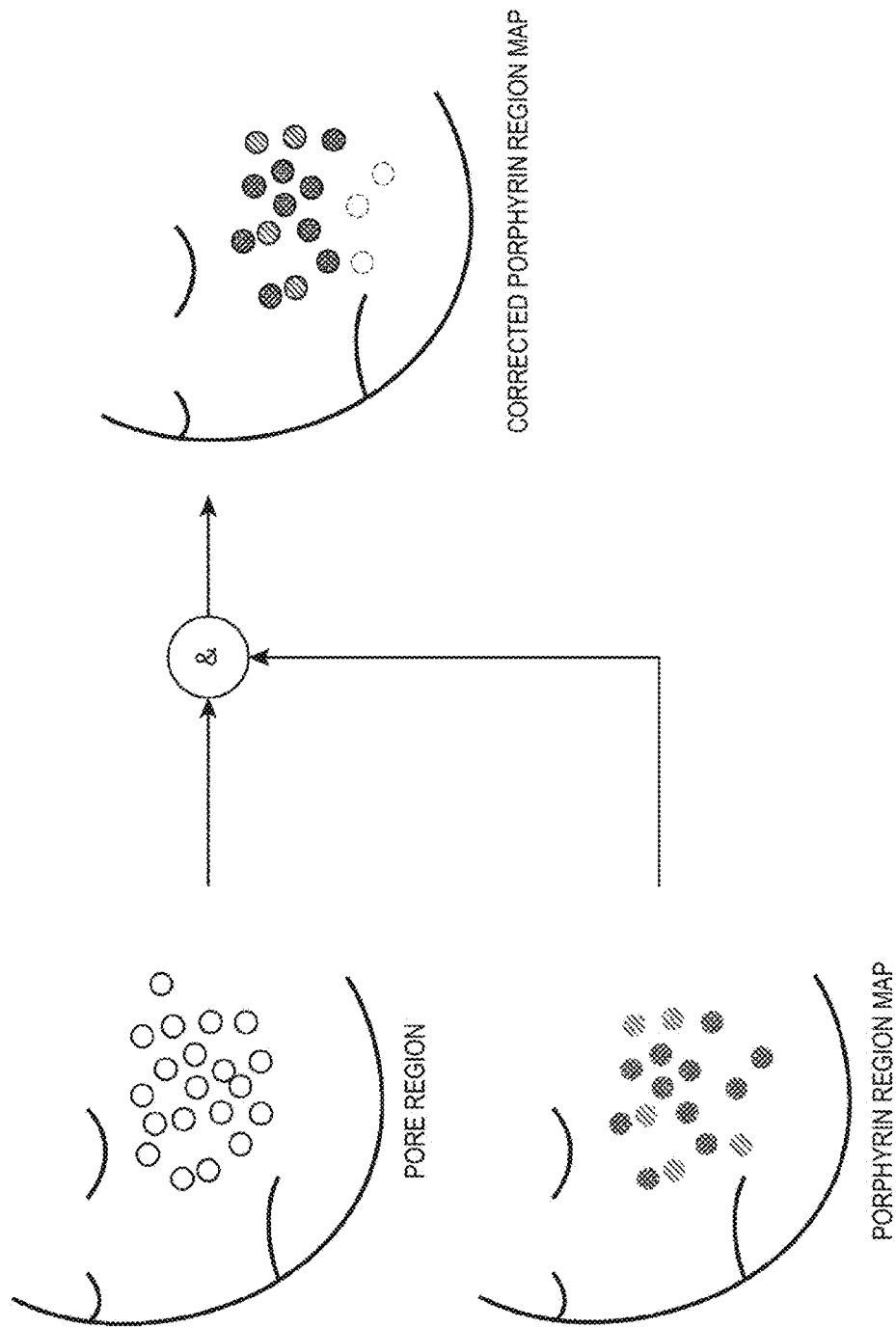
FIG. 26 is a diagram for describing a method of correcting a porphyrin region map.

For example, an upper left drawing in FIG. 26 schematically illustrates an example of the pore region map, a lower left drawing schematically illustrates an example of the porphyrin region map, and a right drawing schematically illustrates an example a corrected porphyrin region map. In this example, the porphyrin region and the porphyrin precursor region indicated by dotted-line circles in the corrected porphyrin region map have no corresponding pore region in the pore region map and are thus deleted from the porphyrin region map.

A phenomenon in which the porphyrin region and the porphyrin precursor region in which there is no corresponding pore region are detected is considered to occur, for example, due to a difference in an irradiation state between the white light and the UV light. Thus, it is desirable that the irradiation states (for example, the irradiation region, the irradiation direction, and the like) of the white light and the UV light match as closely as possible.

The map correcting unit 241 supplies the corrected porphyrin region map to the number-of-porphyrins counting unit 142 and the display control unit 114.

Thereafter, in step S204, similarly to the process of step S3 of FIG. 3, the statistical process is performed, and in step S205, similarly to the process of step S4 of FIG. 3, the analysis result is displayed, and the analysis process ends.

Thus, since the pore detection process and the porphyrin detection process can be performed in parallel, the process can be performed at a high speed.

When an element of the skin other than pores (for example, a texture, a color, or the like) is analyzed, it is desirable to perform the pore detection process first. In other words, the white-light skin image obtained in the pore detection process can be used for analysis of an element of the skin other than pores such as a texture or a color, whereas the UV-light skin image obtained by the porphyrin detection process is used only in the porphyrin detection process. Thus, for example, when the porphyrin detection is not performed, it is desirable to perform the pore detection process before the porphyrin detection process so that the photography of the UV-light skin image can be omitted.

<3. Modified Examples>

Next, modified examples of the embodiments of the present technology will be described.

[First Modified Example: Modified Example Related to Distribution of Functions]

The distribution of the functions of the respective devices in the analysis system illustrated in FIGS. 2 and 23 is an example and can be freely changed.

Figure 27:
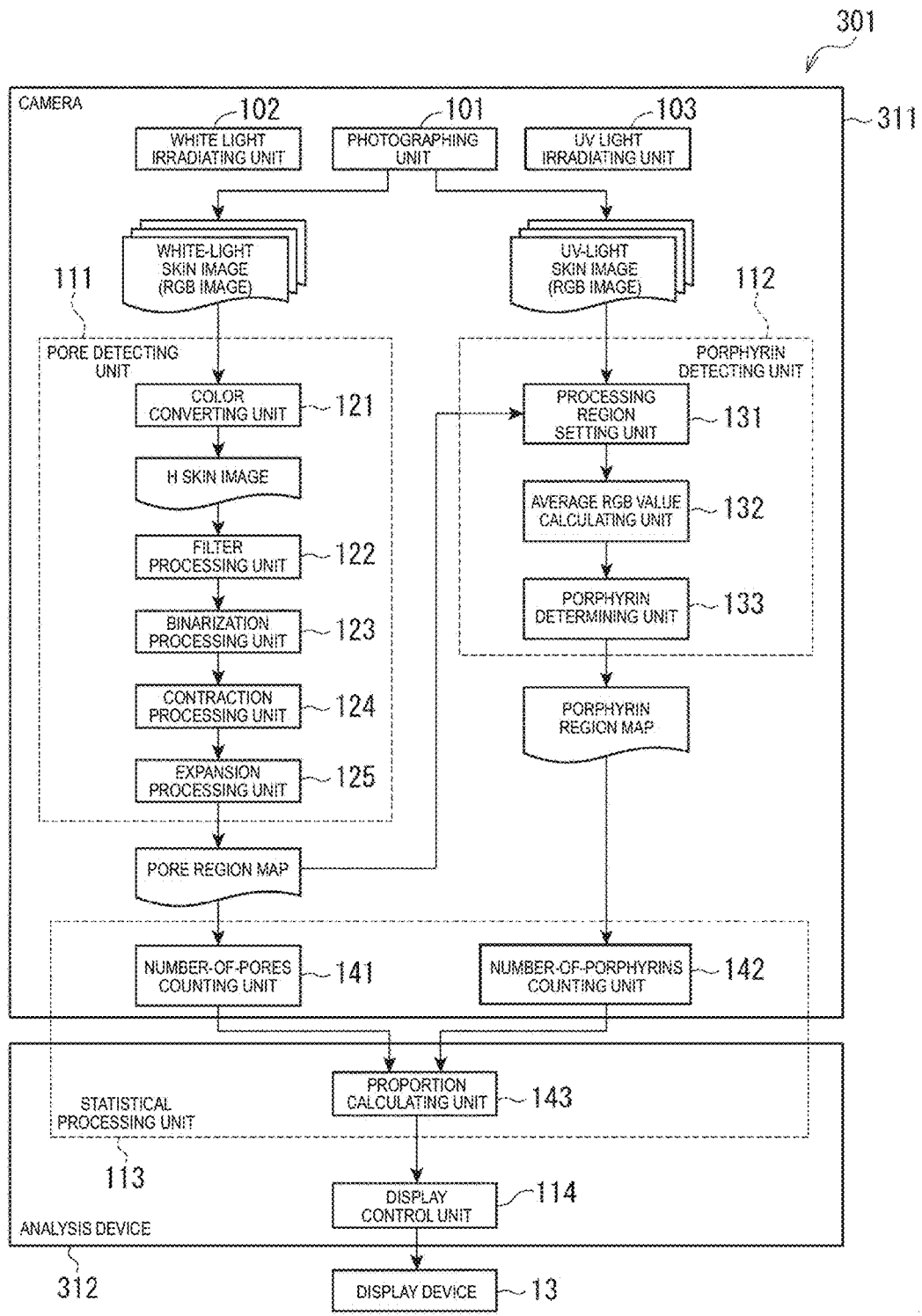
FIG. 27 is a block diagram illustrating an analysis system according to a modified example of the first embodiment.

For example, an analysis system 301 of FIG. 27 is a system in which the distribution of the functions in the analysis system 1 of FIG. 2 is changed. In FIG. 27, parts corresponding to those in FIG. 2 are denoted by the same reference numerals, and repeated description of parts in which processing is the same will be appropriately omitted.

The analysis system 301 differs from the analysis system 1 in that a camera 311 and an analysis device 312 are disposed instead of the camera 11 and the analysis device 12.

The camera 311 has a configuration in which the pore detecting unit 111 and the porphyrin detecting unit 112, and the number-of-pores counting unit 141 and the number-of-porphyrins counting unit 142 of the statistical processing unit 113 which are included in the analysis device 12 are added to the camera 11. On the other hand, the analysis device 312 has a configuration in which the pore detecting unit 111, the porphyrin detecting unit 112, the number-of-pores counting unit 141, and the number-of-porphyrins counting unit 142 of the statistical processing unit 113 are omitted from the analysis device 12.

In the analysis system 301, the process of counting the number of pores, the number of porphyrins, and the number of porphyrin precursors is performed at the camera 311 side, and the counting result is transmitted from the camera 311 to the analysis device 312.

Further, the analysis device 312 calculates the proportion of each type of pore of the user, and causes the calculation result to be displayed on the display device 13. For example, the right graph of FIG. 16, the right graph of FIG. 18, the screens of FIGS. 20 to 22 are displayed.

Thus, in the analysis system 301, transfer of the skin image having a large data amount from the camera 311 to the analysis device 312 may be omitted.

The same distribution of the functions as in the analysis system 301 can be performed in the analysis system 201 of FIG. 23.

Figure 28:
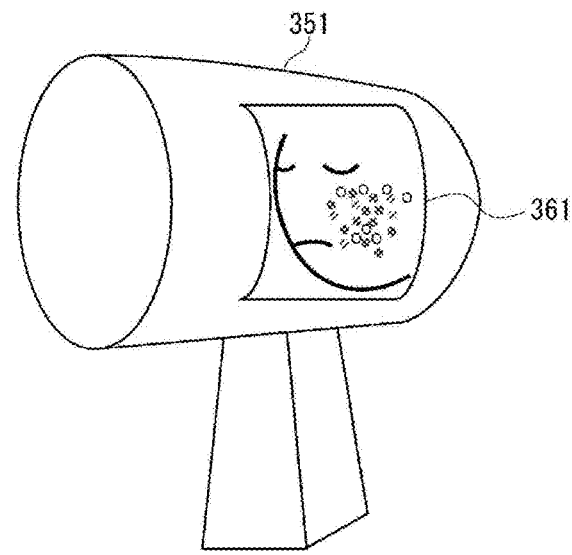
FIG. 28 is a diagram illustrating a camera according to a modified example.

For example, a camera 351 may have all the functions illustrated in FIG. 28. In other words, the camera 351 have all the functions of the camera 11, the analysis device 12, and the display device 13 of FIG. 2 or all the functions of the camera 11, the analysis device 211, and the display device 13 of FIG. 23. Thus, the camera 351 photographs the skin of the user, analyzes the skin state of the user based on the skin image obtained as a result, and causes an analysis result to be displayed on a display unit 361.

Although not illustrated, the analysis device 12 of FIG. 2 or the analysis device 211 of FIG. 23 may have the function of the display device 13, or the camera 11 may have the function of the analysis device 12 of FIG. 2 or the analysis device 211 of FIG. 23.

[Second Modified Example: Modified Example Related to Process]

The example in which the image (the H skin image) of the H (hue) component in the HSV color space is used in the pore detection process has been described above, but an image in any other color space may be used. For example, an original RGB image may be used without change, or an image indicated by a hue angle h obtained by the following Formula (10) for color coordinates a* and b* of an L*a*b* color coordinate system may be used.

$$h=\tan^{-1}(b^*/a^*) \qquad (10)$$

For example, when the analysis result is displayed, the pore in which a porphyrin precursor is detected may be included in the normal pore, and only the pore in which a porphyrin is detected and the normal pore are distinguished and displayed.

For example, the analysis result of the pore state may be displayed together with an analysis result of another element of the skin.

Further, the present technology can also be applied when pores in which an abnormality is detected due to an element other than porphyrins or porphyrin precursors (for example, pores filled with sebum or the like) are detected, and a detection result is displayed. For example, the display methods of FIG. 16 and FIGS. 18 to 22 or the like can be applied.

Although the example in which the pores are detected based on the skin image photographed using the white light, and the pore state is detected based on the skin image photographed using the UV light has been described above, light having other wavelength bands may be used. When light having different wavelength bands is used, a wavelength band of illumination light used for photography of an image used for detection of pores is assumed to be typically different from a wavelength band of illumination light used for photography of an image used for detection of a state of pores.

Further, the example in which the porphyrins and the porphyrin precursors are detected using the R, G, and B components of each of the pixels of the UV-light skin image has been described, but the porphyrins and the porphyrin precursors may be detected using one or two of the R, G, and B components. The porphyrins and the porphyrin precursors may be detected using an image of a color space (for example, the HSV color space) different from the RGB.

{Configuration Example of Computer}

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 29:
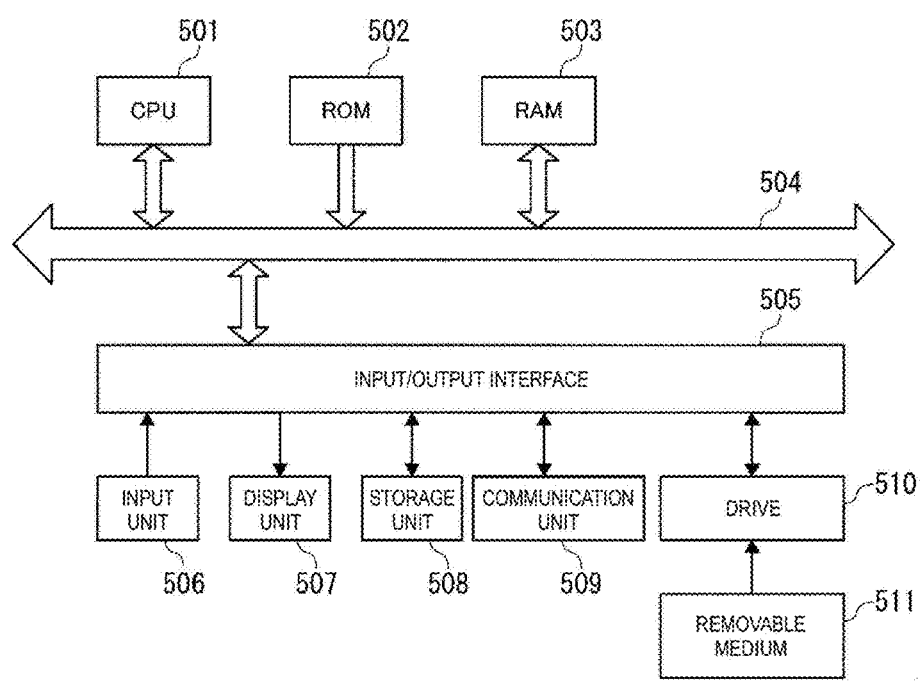
FIG. 29 is a block diagram illustrating an example configuration of a computer.

FIG. 29 is a block diagram showing an example configuration of the hardware of a computer that executes the series of processes described earlier according to a program.

In a computer, a CPU (Central Processing Unit) 501, a ROM (Read Only Memory) 502, and a RAM (Random Access Memory) 503 are mutually connected by a bus 504.

An input/output interface 505 is also connected to the bus 504. An input unit 506, an output unit 507, a storage unit 508, a communication unit 509, and a drive 510 are connected to the input/output interface 505.

The input unit 506 is configured from a keyboard, a mouse, a microphone or the like. The output unit 507 configured from a display, a speaker or the like. The storage unit 508 is configured from a hard disk, a non-volatile memory or the like. The communication unit 509 is configured from a network interface or the like. The drive 910 drives a removable medium 511 such as a magnetic disk, an optical disk, a magneto-optical disk, a semiconductor memory or the like.

In the computer configured as described above, as one example the CPU 501 loads a program stored in the storage unit 508 via the input/output interface 505 and the bus 504 into the RAM 503 and executes the program to carry out the series of processes described earlier.

As one example, the program executed by the computer (the CPU 501) may be provided by being recorded on the removable medium 511 as a packaged medium or the like. The program can also be provided via a wired or wireless transfer medium, such as a local area network, the Internet, or a digital satellite broadcast.

In the computer, by loading the removable medium 511 into the drive 510, the program can be installed into the storage unit 508 via the input/output interface 505. It is also possible to receive the program from a wired or wireless transfer medium using the communication unit 509 and install the program into the storage unit 508. As another alternative, the program can be installed in advance into the ROM 502 or the storage unit 508.

Note that the program executed by the computer may be a program in which processes are carried out in a time series in the order described in this specification or may be a program in which processes are carried out in parallel or at necessary timing, such as when the processes are called.

Further, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a plurality of modules within a single casing.

An embodiment of the disclosure is not limited to the embodiments described above, and various changes and modifications may be made without departing from the scope of the disclosure.

For example, the present disclosure can adopt a configuration of cloud computing which processes by allocating and connecting one function by a plurality of apparatuses through a network.

Further, each step described by the above-mentioned flow charts can be executed by one apparatus or by allocating a plurality of apparatuses.

In addition, in the case where a plurality of processes are included in one step, the plurality of processes included in this one step can be executed by one apparatus or by sharing a plurality of apparatuses.

Note that the effects described in the present specification are merely examples, and not limitative; other effects may be exhibited.

Additionally, the present technology may also be configured as below.

(1)

An information processing device, including:

a display control unit configured to distinguish pores in which an abnormality is detected and normal pores based on a detection result of pores and a pore state of skin of a person and control display of the pore state of the skin of the person.

(2)

The information processing device according to (1), wherein the display control unit distinguishes the pores in which an abnormality is detected and the normal pores and controls display of a pore state image, which is an image indicating the pore state of the skin of the person.

(3)

The information processing device according to (2), wherein the pores in which an abnormality is detected include at least one of pores in which porphyrins are detected and pores in which porphyrin precursors are detected.

(4)

The information processing device according to (3), wherein the display control unit performs control such that the pore state image is displayed so that the pores in which porphyrins are detected and the pores in which the porphyrin precursors are detected are distinguished.

(5)

The information processing device according to (3), wherein the display control unit performs control such that the pore state image is displayed so that the pores in which porphyrins are detected and the pores in which the porphyrin precursors are detected are not distinguished.

(6)

The information processing device according to any one of (2) to (5), wherein the display control unit performs control such that only pores of a selected type are displayed in the pore state image.

(7)

The information processing device according to (1), wherein the pores in which an abnormality is detected may include at least one of pores in which porphyrins are detected and pores in which porphyrin precursors are detected.

(8)

The information processing device according to (7), wherein the display control unit controls display of a graph indicating proportions of pores in which porphyrins and porphyrin precursors are detected and the normal pores or a graph indicating proportions of the pores in which porphyrins are detected, the pores in which porphyrin precursors are detected, and the normal pores.

(9)

The information processing device according to (8), wherein the display control unit performs control such that pores of a selected type in the graph are highlighted in a pore state image, which is an image indicating the state of the pores in the skin of the person.

(10)

The information processing device according to any one of (7) to (9),
wherein the display control unit performs control such that a graph having an axis indicating a porphyrin rate, which is a proportion of the pores in which porphyrins are detected, and an axis indicating a porphyrin precursor rate, which is a proportion of the pores in which porphyrin precursors are detected, is displayed, and positions on the graph corresponding to the porphyrin rate and the porphyrin precursor rate of the user are displayed.

(11)

The information processing device according to any one of (7) to (9),
wherein the display control unit controls display of a graph indicating transition of a statistic related to at least one of the pores in which porphyrins are detected, the pores in which porphyrin precursors are detected, and the normal pores.

(12)

The information processing device according to any one of (1) to (11), further including:
a pore detecting unit configured to detect pores in a first skin image, which is an image obtained by photographing the skin of the person irradiated with first light of a first wavelength band; and
a state detecting unit configured to detect the pore state of the skin of the person based on pixel values of a plurality of color components of a second skin image obtained by photographing the skin of the person irradiated with second light of a second wavelength band different from the first wavelength band.

(13)

The information processing device according to (12),
wherein the first light is white light,
the second light is UV light, and
the state detecting unit detects porphyrins and porphyrin precursors based on pixel values of R, G, and B components of each of pixels of the second skin image.

(14)

The information processing device according to (13),
wherein the state detecting unit determines that the porphyrins are generated in a region in which the pixel value of the R component is relatively larger than the pixel value of the G component and the pixel value of the G component is relatively larger than the pixel value of the B component among regions of the second skin image corresponding to pores detected in the first skin image, and determines that the porphyrin precursors are generated in a region in which the pixel value of the R component is substantially equal to the pixel value of the G component and the pixel values of the R component and the G component are relatively larger than the pixel value of the B component.

(15)

The information processing device according to (13),
wherein the state detecting unit determines that the porphyrins are generated in a region in which the pixel value of the R component is relatively larger than the pixel value of the G component and the pixel value of the G component is relatively larger than the pixel value of the B component among regions in which pixels of a chromatic color are concentrated in the second skin image, and determines that the porphyrin precursors are generated in a region in which the pixel value of the R component is substantially equal to the pixel value of the G component and the pixel values of the R component and the G component are relatively larger than the pixel value of the B component.

(16)

The information processing device according to (15), further including:
a correcting unit configured to delete a region in which no pores are detected in the first skin image from the region in which the porphyrins or the porphyrin precursors are determined to be generated.

(17)

A program causing a computer to execute a process including:
a display control step of distinguishing pores in which an abnormality is detected and normal pores based on a detection result of pores and a pore state of skin of a person and controlling display of the pore state of the skin of the person.

(18)

An information processing system, including:
a photographing unit configured to photograph skin of a person irradiated with first light of a first wavelength band or second light of a second wavelength band different from the first wavelength band;
a pore detecting unit configured to detect pores in a first skin image, which is an image obtained by photographing the skin of the person irradiated with the first light;
a state detecting unit configured to detect a pore state of the skin of the person based on pixel values of a plurality of color components of each of pixels of a second skin image, which is an image obtained by photographing the skin of the person irradiated with second light; and
a display control unit configured to distinguish pores in which an abnormality is detected and normal pores based on a detection result of the pores and the pore state of the skin of the person and control display of the pore state of the skin of the person.

(19)

The information processing system according to (18),
wherein the display control unit distinguishes the pores in which an abnormality is detected and the normal pores and controls display of a pore state image, which is an image indicating the pore state of the skin of the person.

(20)

The information processing system according to (19), further including:
a display unit configured to display the pore state image.

(21)

The information processing system according to any one of (18) to (20),
wherein the first light is white light,
the second light is UV light,
the state detecting unit detects porphyrins and porphyrin precursors based on pixel values of R, G, and B components of each of pixels of the second skin image, and
the display control unit distinguishes between the normal pores and at least one of pores in which porphyrins are detected and pores in which porphyrin precursors are detected based on a detection result of porphyrins and porphyrin precursors of the skin of the person, and controls display of the pore state of the skin of the person.

(22)

The information processing system according to (21),
wherein the state detecting unit determines that the porphyrins are generated in a region in which the pixel value of the R component is relatively larger than the pixel value of the G component and the pixel value of the G component is relatively larger than the pixel value of the B component among regions of the second skin image corresponding to pores detected in the first skin image, and determines that the porphyrin precursors are generated in a region in which the pixel value of the R component is substantially equal to the pixel value of the G component and the pixel values of the R component and the G component are relatively larger than the pixel value of the B component.

(23) The information processing system according to (21), wherein the state detecting unit determines that the porphyrins are generated in a region in which the pixel value of the R component is relatively larger than the pixel value of the G component and the pixel value of the G component is relatively larger than the pixel value of the B component among regions in which pixels of a chromatic color are concentrated in the second skin image, and determines that the porphyrin precursors are generated in a region in which the pixel value of the R component is substantially equal to the pixel value of the G component and the pixel values of the R component and the G component are relatively larger than the pixel value of the B component.

(24) The information processing system according to any one of (18) to (23), including:
a photographing device including at least the photographing unit; and
an information processing device including at least the display control unit,
wherein the pore detecting unit and the state detecting unit are included in the photographing device or the information processing device.

(25) An information processing system, including:
a photographing device including a photographing unit, a pore detecting unit, a porphyrin detecting unit, and a counting unit; and
an information processing device including a display control unit,
wherein the photographing unit photographs skin of a person irradiated with white light or UV light having a predetermined wavelength,
the pore detecting unit detects pores in a first skin image, which is an image obtained by photographing the skin of the person irradiated with the white light,
the porphyrin detecting unit detects porphyrins and porphyrin precursors based on pixel values of R, G, and B components of each of pixels of a second skin image, which is an image obtained by photographing the skin of the person irradiated with the UV light,
the counting unit counts the number of detected pores, the number of porphyrins, and the number of porphyrin precursors, and
the display control unit controls display of data based on the number of pores, the number of porphyrins, and the number of porphyrin precursors.

REFERENCE SIGNS LIST 1 analysis system
11 camera
12 analysis device
13 display device
101 photographing unit
102 white light irradiating unit
103 UV light irradiating unit
104 pore detecting unit
105 porphyrin detecting unit
106 statistical processing unit
107 display control unit
121 color converting unit
122 filter processing unit
123 binarization processing unit
124 contraction processing unit
125 expansion processing unit
131 processing region setting unit
132 average RGB value calculating unit
133 porphyrin determining unit
141 number-of-pores counting unit
142 number-of-porphyrins counting unit
143 proportion calculating unit
201 analysis system
211 analysis device
221 porphyrin detecting unit
222 statistical processing unit
231 processing region setting unit

The invention claimed is:

1. An information processing device, comprising:
a photographing unit configured to photograph skin of a person irradiated with first light of a first wavelength band or second light of a second wavelength band different from the first wavelength band; and
processing circuitry including at least one processor and a memory storing instructions that, when executed by the processor, implement:
a pore detecting unit configured to detect pores in a first skin image, which is an image obtained by photographing the skin of a person irradiated with the first light of the first wavelength band;
a state detecting unit configured to detect a pore state of the skin of the person based on pixel values of a plurality of color components of a second skin image obtained by photographing the skin of the person irradiated with the second light of the second wavelength band different from the first wavelength band; and
a display control unit configured to distinguish pores in which an abnormality is detected and normal pores based on the detected pores and the detected pore state of the skin of the person and to control display of the pore state of the skin of the person, wherein the display control unit controls display of a pore state image which distinguishes pores in which an abnormality is detected and normal pores, wherein the first light is white light, the second light is UV light, and the state detecting unit detects porphyrins and porphyrin precursors based on pixel values of R, G, and B components of each of pixels of the second skin image.

2. The information processing device according to claim 1,
wherein the pores in which an abnormality is detected include at least one of pores in which porphyrins are detected and pores in which porphyrin precursors are detected.

3. The information processing device according to claim 2,
wherein the display control unit performs control such that the pore state image is displayed so that the pores in which porphyrins are detected and the pores in which the porphyrin precursors are detected are distinguished.

4. The information processing device according to claim 2,
wherein the display control unit performs control such that the pore state image is displayed so that the pores in which porphyrins are detected and the pores in which the porphyrin precursors are detected are not distinguished.

5. The information processing device according to claim 1,
   wherein the display control unit performs control such that only pores of a selected type are displayed in the pore state image.

6. The information processing device according to claim 1,
   wherein the pores in which an abnormality is detected may include at least one of pores in which porphyrins are detected and pores in which porphyrin precursors are detected.

7. The information processing device according to claim 6,
   wherein the display control unit controls display of a graph indicating proportions of pores in which porphyrins and porphyrin precursors are detected and the normal pores or a graph indicating proportions of the pores in which porphyrins are detected, the pores in which porphyrin precursors are detected, and the normal pores.

8. The information processing device according to claim 7,
   wherein the display control unit performs control such that pores of a selected type in the graph are highlighted in a pore state image, which is an image indicating the state of the pores in the skin of the person.

9. The information processing device according to claim 6,
   wherein the display control unit performs control such that a graph having an axis indicating a porphyrin rate, which is a proportion of the pores in which porphyrins are detected, and an axis indicating a porphyrin precursor rate, which is a proportion of the pores in which porphyrin precursors are detected, is displayed, and positions on the graph corresponding to the porphyrin rate and the porphyrin precursor rate of the user are displayed.

10. The information processing device according to claim 6,
    wherein the display control unit controls display of a graph indicating transition of a statistic related to at least one of the pores in which porphyrins are detected, the pores in which porphyrin precursors are detected, and the normal pores.

11. The information processing device according to claim 1,
    wherein the state detecting unit determines that the porphyrins are generated in a region in which the pixel value of the R component is relatively larger than the pixel value of the G component and the pixel value of the G component is relatively larger than the pixel value of the B component among regions of the second skin image corresponding to pores detected in the first skin image, and determines that the porphyrin precursors are generated in a region in which the pixel value of the R component is substantially equal to the pixel value of the G component and the pixel values of the R component and the G component are relatively larger than the pixel value of the B component.

12. The information processing device according to claim 1,
    wherein the state detecting unit determines that the porphyrins are generated in a region in which the pixel value of the R component is relatively larger than the pixel value of the G component and the pixel value of the G component is relatively larger than the pixel value of the B component among regions in which pixels of a chromatic color are concentrated in the second skin image, and determines that the porphyrin precursors are generated in a region in which the pixel value of the R component is substantially equal to the pixel value of the G component and the pixel values of the R component and the G component are relatively larger than the pixel value of the B component.

13. The information processing device according to claim 12, further comprising:
    a correcting unit configured to delete a region in which no pores are detected in the first skin image from the region in which the porphyrins or the porphyrin precursors are determined to be generated.

14. A non-transitory computer-readable medium storing computer-executable instructions that, when executed by a computer, perform a process comprising:
    detecting, by the computer, pores in a first skin image, which is an image obtained by photographing, by a photographing unit, the skin of a person irradiated with first light of a first wavelength band;
    detecting, by the computer, a pore state of the skin of the person based on pixel values of a plurality of color components of a second skin image obtained by photographing, by the photographing unit, the skin of the person irradiated with second light of a second wavelength band different from the first wavelength band; and
    distinguishing, by the computer, pores in which an abnormality is detected and normal pores based on the detected pores and the detected pore state of the skin of the person and controlling display of the pore state of the skin of the person, wherein controlling display of the pore state includes controlling display of a pore state image which distinguishes pores in which an abnormality is detected and normal pores, wherein the first light is white light, the second light is UV light, and the pore state detecting includes detecting porphyrins and porphyrin precursors based on pixel values of R, G, and B components of each of pixels of the second skin image.

15. An information processing system, comprising:
    a photographing unit configured to photograph skin of a person irradiated with first light of a first wavelength band or second light of a second wavelength band different from the first wavelength band; and
    processing circuitry including at least one processor and a memory storing instructions that, when executed by the processor, implement:
    a pore detecting unit configured to detect pores in a first skin image, which is an image obtained by photographing the skin of the person irradiated with the first light;
    a state detecting unit configured to detect a pore state of the skin of the person based on pixel values of a plurality of color components of each of pixels of a second skin image, which is an image obtained by photographing the skin of the person irradiated with second light; and
    a display control unit configured to distinguish pores in which an abnormality is detected and normal pores based on the detected pores and the detected pore state of the skin of the person and to control display of the pore state of the skin of the person, wherein the display control unit controls display of a pore state image which distinguishes pores in which an abnormality is detected and normal pores, wherein the first light is white light, the second light is UV light, the state detecting unit detects porphyrins and porphyrin precursors based on pixel values of R, G, and B components of each of pixels of the second skin image, and the display control unit distinguishes between the normal pores and at least one of pores in which porphyrins are detected and pores in which porphyrin precursors are detected based on a detection result of porphyrins and porphyrin precursors of the skin of the person, and controls display of the pore state of the skin of the person.

16. The information processing system according to claim 15,
wherein the state detecting unit determines that the porphyrins are generated in a region in which the pixel value of the R component is relatively larger than the pixel value of the G component and the pixel value of the G component is relatively larger than the pixel value of the B component among regions of the second skin image corresponding to pores detected in the first skin image, and determines that the porphyrin precursors are generated in a region in which the pixel value of the R component is substantially equal to the pixel value of the G component and the pixel values of the R component and the G component are relatively larger than the pixel value of the B component.

17. The information processing system according to claim 15,
wherein the state detecting unit determines that the porphyrins are generated in a region in which the pixel value of the R component is relatively larger than the pixel value of the G component and the pixel value of the G component is relatively larger than the pixel value of the B component among regions in which pixels of a chromatic color are concentrated in the second skin image, and determines that the porphyrin precursors are generated in a region in which the pixel value of the R component is substantially equal to the pixel value of the G component and the pixel values of the R component and the G component are relatively larger than the pixel value of the B component.

18. The information processing system according to claim 15, comprising:
a photographing device including at least the photographing unit; and
an information processing device including at least the display control unit,
wherein the pore detecting unit and the state detecting unit are included in the photographing device or the information processing device.

19. An information processing system, comprising:
a photographing device comprising first processing circuitry including at least one processor and a memory storing instructions that, when executed by the processor, implement a photographing unit, a pore detecting unit, a porphyrin detecting unit, and a counting unit; and
an information processing device comprising second processing circuitry including at least one processor and a memory storing instructions that, when executed by the processor, implement a display control unit,
wherein the photographing unit photographs skin of a person irradiated with white light or UV light having a predetermined wavelength,
the pore detecting unit detects pores in a first skin image, which is an image obtained by photographing the skin of the person irradiated with the white light,
the porphyrin detecting unit detects porphyrins and porphyrin precursors based on pixel values of R, G, and B components of each of pixels of a second skin image, which is an image obtained by photographing the skin of the person irradiated with the UV light,
the counting unit counts the number of detected pores, the number of porphyrins, and the number of porphyrin precursors, and
the display control unit controls display of data based on the number of pores, the number of porphyrins, and the number of porphyrin precursors.

* * * * *